US012700364B2

(12) United States Patent
Kim

(10) Patent No.: US 12,700,364 B2
(45) Date of Patent: Aug. 4, 2026

(54) DISPLAY DEVICE FOR PROVIDING BIOMETRIC INFORMATION USING INFRARED LIGHT

(71) Applicant: SAMSUNG DISPLAY CO., LTD., Yongin-si (KR)

(72) Inventor: Chul Kim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 19/046,935

(22) Filed: Feb. 6, 2025

(65) Prior Publication Data

US 2025/0182695 A1      Jun. 5, 2025

Related U.S. Application Data

(63) Continuation of application No. 18/187,458, filed on Mar. 21, 2023, now Pat. No. 12,249,281.

(30) Foreign Application Priority Data

Aug. 2, 2022     (KR) ........................ 10-2022-0096088

(51) Int. Cl.
G06F 3/045 (2006.01)
G06F 3/044 (2006.01)
(Continued)

(52) U.S. Cl.
CPC ......... G09G 3/3233 (2013.01); G06F 3/0446 (2019.05); G06V 40/15 (2022.01);
(Continued)

(58) Field of Classification Search
CPC ..... G09G 3/3233; G06F 3/0446; G06V 40/15
(Continued)

(56) References Cited

U.S. PATENT DOCUMENTS 10,388,706 B2     8/2019  Lee et al.
10,398,324 B2     9/2019  Mukkamala et al.
(Continued)

FOREIGN PATENT DOCUMENTS

KR     10-2018-0103206 A     9/2018
KR     10-2019-0030809 A     3/2019
(Continued)

OTHER PUBLICATIONS

Claire Lochner, "Printed Organic Light Emitting Diodes for Biomedical Applications", Technical Report to UCB/EECS-2020-31, May 1, 2020, http://www2.eecs.berkley.edu/Pubs/TechRpts/2020/EECS-2020-31.html.
(Continued)

*Primary Examiner* — Jonathan M Blancha
(74) *Attorney, Agent, or Firm* — F. CHAU & ASSOCIATES, LLC

(57)      ABSTRACT

A display device includes display pixels arranged in a display area of a display panel, infrared light emitting pixels arranged in the display area to alternate with the display pixels, light sensing pixels arranged in the display area to alternate with the infrared light emitting pixels, a display scan driver supplying display scan signals to the display pixels and the infrared light emitting pixels, a light sensing driver sequentially supplying sensing scan signals to the light sensing pixels, and a component detection circuit for analyzing biomarker information using light sensing signals received from the light sensing pixels, which are based on light reflected from an object in front of the display panel.

20 Claims, 24 Drawing Sheets

(51) Int. Cl.

| | |
|---|---|
| *G06V 40/10* | (2022.01) |
| *G09G 3/3233* | (2016.01) |
| *H10K 39/34* | (2023.01) |
| *A61B 5/00* | (2006.01) |
| *H10K 59/10* | (2023.01) |

(52) U.S. Cl.
CPC ............ *H10K 39/34* (2023.02); *A61B 5/0075* (2013.01); *G09G 2300/0452* (2013.01); *G09G 2300/0842* (2013.01); *G09G 2300/0861* (2013.01); *G09G 2310/08* (2013.01); *G09G 2354/00* (2013.01); *G09G 2360/14* (2013.01); *H10K 59/10* (2023.02)

(58) Field of Classification Search
USPC ......................................................... 345/174
See application file for complete search history.

(56) References Cited

U.S. PATENT DOCUMENTS

| | | | |
|---|---|---|---|
| 10,505,134 B2 | 12/2019 | Choi et al. | |
| 10,712,851 B2 | 7/2020 | Heo et al. | |
| 10,985,220 B2 | 4/2021 | Lee et al. | |
| 11,281,320 B2 | 3/2022 | Heo et al. | |
| 11,842,002 B2 | 12/2023 | Takahashi et al. | |
| 2017/0199610 A1* | 7/2017 | Kitchens, II | G06V 10/811 |
| 2019/0013368 A1 | 1/2019 | Chung et al. | |
| 2019/0302937 A1 | 10/2019 | Heo et al. | |
| 2020/0111851 A1* | 4/2020 | Park | G06F 3/0412 |
| 2020/0243620 A1* | 7/2020 | Abe | H10K 50/841 |
| 2021/0038144 A1 | 2/2021 | Watanabe | |
| 2021/0158751 A1 | 5/2021 | Cha et al. | |
| 2022/0214803 A1* | 7/2022 | Trapero Martin | G04G 21/025 |
| 2022/0328571 A1* | 10/2022 | Kurokawa | H10K 59/65 |
| 2022/0350432 A1* | 11/2022 | Takahashi | H10K 30/88 |
| 2024/0046869 A1 | 2/2024 | Kim | |
| 2024/0138169 A1* | 4/2024 | Kusunoki | G09G 3/3233 |

FOREIGN PATENT DOCUMENTS

| | | |
|---|---|---|
| KR | 10-2019-0114644 A | 10/2019 |
| KR | 10-2021-0064483 A | 6/2021 |
| KR | 10-2022-0043390 A | 4/2022 |
| WO | 2021064509 A1 | 4/2021 |
| WO | 2021116766 A1 | 6/2021 |

OTHER PUBLICATIONS

Nina Sviridova, et al., "Photoplehsmogram at green: Where does chaos arise from?", Chaos, Solitions and Fractals 116(2018) 157-165.

Jorge Blasco et al., "On the Feasibility of Low-Cost Wearable Sensors for Multi-Modal Biometric Verification", Sensors 2018, www.mdpi.com/journal/sensors.

Office Action dated May 15, 2024 cited in related U. Appl. No. 18/187,458.

Notice of Allowance dated Nov. 6, 2024 cited in related U.S. Appl. No. 18/187,458.

Office Action dated Jan. 16, 2026 issued in corresponding Korean Appln No. KR 10-2022-0096088.

* cited by examiner

FIG. 1

DA: FSA1, FSA2, IDA

Figure 20:
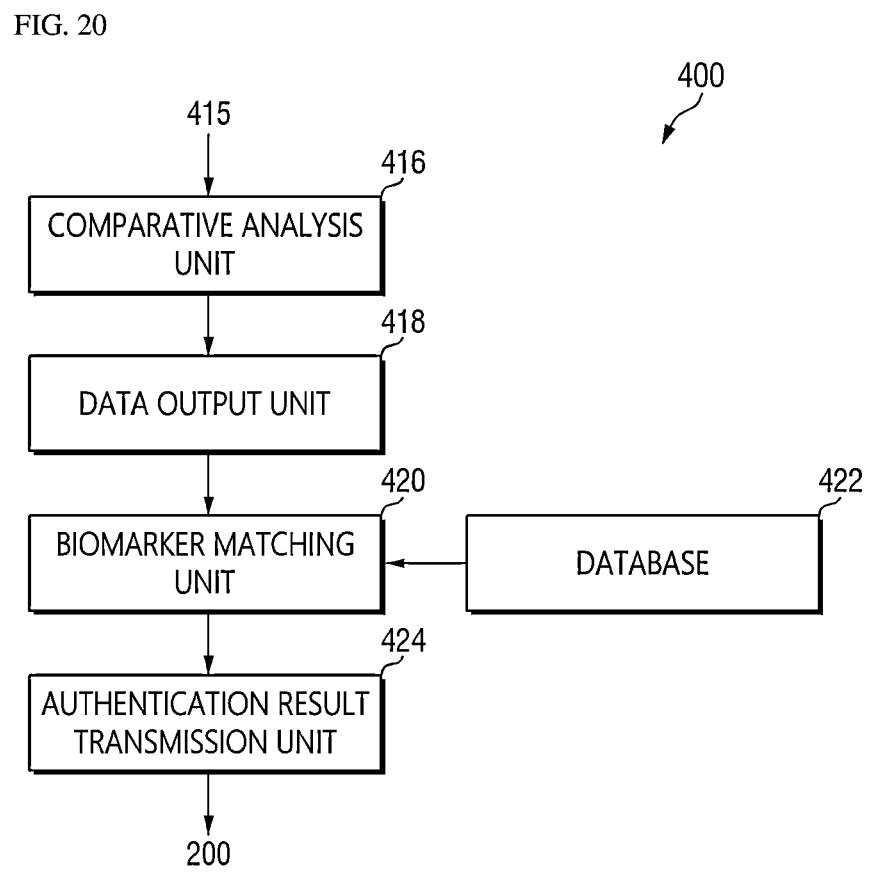

COMPARATIVE ANALYSIS UNIT 416

DATA OUTPUT UNIT 418

BIOMARKER MATCHING UNIT 420 ← DATABASE 422

AUTHENTICATION RESULT TRANSMISSION UNIT 424

NDA2

DA2

NFA2

DR3

DR2

DR1

DISPLAY DEVICE FOR PROVIDING BIOMETRIC INFORMATION USING INFRARED LIGHT

CROSS-REFERENCE TO RELATED APPLICATION

This U.S. non-provisional patent application is a continuation application of U.S. patent application Ser. No. 18/187,458 filed Mar. 21, 2023, which claims priority under 35 U.S.C. § 119 to Korean Patent Application No. 10-2022-0096088, filed on Aug. 2, 2022, in the Korean Intellectual Property Office, the disclosures of which are incorporated by reference in their entirety herein.

1. TECHNICAL FIELD

The present disclosure relates to a display device.

2. DISCUSSION OF RELATED ART

As the information society develops, demands for display devices for displaying images are increasing in various forms. Display devices are being applied to various electronic devices such as smartphones, digital cameras, laptop computers, tablet personal computers (PCs), navigation devices, and smart televisions. A portable display device such as a smartphone or a tablet PC is equipped with various functions such as image capturing, fingerprint recognition, and face recognition.

In recent years, devices for acquiring biometric information such as skin moisture level or blood pressure and component information of fruit or vegetables in an oscillometric method using a photosensor have been developed.

A measuring device may use the photosensor to detect biometric information of a user. However, since the photosensor requires an independent light source, a sensor and a display device, and a portable smartphone or tablet PC for executing an application program has to be additionally carried. Thus, there is a need for a method for integrating the measuring device using a photosensor and a portable display device.

SUMMARY

At least one embodiment of the present disclosure provides a display device which can detect an optical signal of an infrared wavelength band using an image display panel and extract various component information as well as biometric information using the detected optical signal.

At least one embodiment of the present disclosure provides a display device which can emit infrared light of different wavelength bands using red, green, blue and infrared light sources and extract and utilize various biomarkers by detecting infrared optical signals of different wavelength bands.

According to an embodiment of the disclosure, a display device includes display pixels arranged in a display area of a display panel, infrared light emitting pixels arranged in the display area to alternate with the display pixels, light sensing pixels arranged in the display area to alternate with the infrared light emitting pixels, a display scan driver supplying display scan signals to the display pixels and the infrared light emitting pixels, a light sensing driver sequentially supplying sensing scan signals to the light sensing pixels, and a component detection circuit for generating biomarker information using light sensing signals received from the light sensing pixels. The light sensing signals are based on light reflected from an object in front of the display panel.

In an embodiment, the display area comprises an image display area in which only the display pixels are disposed without the infrared light emitting pixels and the light sensing pixels, and at least one reflected light sensing area in which the display pixels, the infrared light emitting pixels, and the light sensing pixels are alternately disposed.

In an embodiment, in the display area, first and second display pixels respectively displaying red light and green light among the display pixels, one infrared light emitting pixel and one light sensing pixel are arranged to form first unit pixel, and second and third display pixels respectively displaying green light and blue light among the display pixels, one infrared light emitting pixel and one light sensing pixel are arranged to form a second unit pixel.

In an embodiment, the first and second unit pixels are alternately arranged in a zigzag pattern along a first direction and a second direction or are alternately arranged in a matrix along the first direction and the second direction.

In an embodiment, in the display area, first through third display pixels respectively displaying red light, green light and blue light among the display pixels and one infrared light emitting pixel are arranged to form first unit pixel, and the first through third display pixels respectively displaying red light, green light and blue light and one light sensing pixel are arranged to form a second unit pixel.

In an embodiment, the first and second unit pixels are alternately arranged in a zigzag pattern along a first direction and a second direction or are alternately arranged in a matrix along the first direction and the second direction.

In an embodiment, the first unit pixels and the second unit pixels are alternately arranged in a quad structure or a Pentile™ matrix structure along the first and second directions.

In an embodiment, each of the infrared light emitting pixels receives a data voltage of a data wiring according to a display scan signal and an emission control signal from the display scan driver and emits infrared light by supplying a driving current to a light emitting element according to the data voltage, and the data voltage applied to each infrared light emitting pixel is a same voltage as a data voltage applied to each of the display pixels displaying the blue light.

In an embodiment, the light sensing pixels generate the light sensing signals corresponding to amounts the reflected light and transmit the light sensing signals to the component detection circuit by sequentially responding to the sensing scan signals received through light sensing scan wirings.

In an embodiment, the light sensing pixels generate the light sensing signals corresponding to amounts of the reflected light and transmit the light sensing signals to the component detection circuit by sequentially responding to the display scan signals received from the display scan driver through display scan wirings.

In an embodiment, the component detection circuit includes: an analog-to-digital (A2D) converter converting the light sensing signals from the light sensing pixels into digital light sensing signals, a delay circuit storing, delaying and outputting the digital light sensing signals in units of at least one horizontal line or frame, an arithmetic processing unit generating biometric data by performing an arithmetic operation on one of the digital light sensing signal output from the A2D converter and one of the delayed digital light sensing signals output from the delay circuit, a logic circuit or comparator comparing the biometric data with preset biomarker data to generate a comparison result for detecting biomarker information; and a data output circuit sharing the biomarker information with a main driving circuit.

In an embodiment, the main driving circuit controls driving timings of the display pixels, the light emitting pixels and the display scan driver and generates digital video data according to the biomarker information or executes an application program that presents the biomarker information (e.g., in a text or graphic form).

In an embodiment, the component detection circuit further comprises a biomarker matching unit comparing the biomarker information with biomarker information of a user stored in advance (e.g., in a database) and extracting user information of the user in which the biomarker information matches the biomarker information of the user within a preset error range, and an authentication result transmission unit sharing the user information with the main driving circuit.

In an embodiment, the component detection circuit comprises a first A2D converter converting a first light sensing signal received from each light sensing pixel in a first reflected light sensing area of the display area into a digital first light sensing signal, a second AD2 converter converting a second light sensing signal from each light sensing pixel in a second reflected light sensing area of the display area into a digital second light sensing signal, a delay circuit storing, delaying, and outputting at least one of the digital first and second light sensing signals in units of at least one horizontal line or frame, an arithmetic processing unit generating biometric data by performing an arithmetic operation on a digital light sensing signal output from the first A2D converter and at least one of the delayed first and second light sensing signals output from the delay circuit, and a logic circuit comparing the biometric data with a preset biomarker data to generate a comparison result for detecting the biomarker information.

According to an embodiment of the disclosure, a display device includes display pixels arranged in a display area of a display panel, infrared light emitting pixels arranged in the display area to alternate with the display pixels, light sensing pixels arranged in the display area to alternate with the infrared light emitting pixels, a display scan driver supplying display scan signals to the display pixels and the infrared light emitting pixels, a light sensing driver sequentially supplying sensing scan signals to the light sensing pixels, a component detection circuit generate biomarker information using light sensing signals received from the light sensing pixels and based on light reflected from an object in front of the display panel, a touch sensing circuit detecting coordinate data of a touch position of a user through touch electrodes of a touch sensor, and a main driving circuit controlling driving timings of the display pixels, the light emitting pixels, the light sensing driver, and the display scan driver.

In an embodiment, in the display area, first and second display pixels respectively displaying red light and green light among the display pixels, one infrared light emitting pixel and one light sensing pixel are arranged to form a first unit pixel, and second and third display pixels respectively displaying green light and blue light among the display pixels, one infrared light emitting pixel and one light sensing pixel are arranged to form a second unit pixel.

In an embodiment, in the display area, first through third display pixels respectively displaying red light, green light and blue light among the display pixels and one infrared light emitting pixel are arranged to form a first unit pixel, and the first through third display pixels respectively displaying red light, green light and blue light and one light sensing pixel are arranged to form a second unit pixel.

In an embodiment, the light sensing pixels generate the light sensing signals corresponding to amounts of the reflected light incident and transmit the light sensing signals to the component detection circuit by sequentially responding to the sensing scan signals received through light sensing scan wirings.

In an embodiment, the component detection circuit includes an A2D converter converting the light sensing signals from the light sensing pixels into digital light sensing signals, a delay circuit storing, delaying and outputting the digital light sensing signals in units of at least one horizontal line or frame, an arithmetic processing unit generating biometric data by performing an arithmetic operation on a digital light sensing signal output from the A2D converter and a delayed digital light sensing signal output from the delay circuit, a logic circuit comparing the biometric data with preset biomarker data to generate a comparison result for detecting biomarker information, and a data output circuit sharing the biomarker information with the main driving circuit.

In an embodiment, the main driving circuit controls driving timings of the display pixels, the light emitting pixels and the display scan driver and generates digital video data according to the biomarker information or executes an application program that presents the biomarker information (e.g., in text or graphic form).

In display devices according to embodiments, when light emitted from red, green and blue subpixels and infrared light emitting pixels is reflected by an object such as a body part, the reflected light may be sensed using light sensing pixels of a display panel to detect optical signals. Then, the detected optical signals may be analyzed to extract various biomarkers of the object.

A display device according to at least one of the embodiments emits infrared light of different wavelength bands for extracting various biomarkers by detecting infrared optical signals of various wavelength bands. Therefore, application fields and utilization of the display devices can be further increased.

BRIEF DESCRIPTION OF THE DRAWINGS

These and/or other aspects will become apparent and more readily appreciated from the following description of the embodiments, taken in conjunction with the accompanying drawings in which:

FIG. 1 is a perspective view of a display device according to an embodiment;

FIG. 20 is a schematic block diagram of a component detection circuit according to an embodiment;

FIG. 23 illustrates a scalp inspection method using the display device according to the embodiment.

DETAILED DESCRIPTION OF THE EMBODIMENTS

The present invention will now be described more fully hereinafter with reference to the accompanying drawings, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

It will also be understood that when a layer is referred to as being "on" another layer or substrate, it can be directly on the other layer or substrate, or intervening layers may also be present.

The same reference numbers indicate the same components throughout the specification.

It will be understood that, although the terms "first," "second," etc. may be used herein to describe various elements, these elements should not be limited by these terms. These terms are only used to distinguish one element from another element. For instance, a first element discussed below could be termed a second element without departing from the teachings of the present invention. Similarly, the second element could also be termed the first element.

Each of the features of the various embodiments of the present disclosure may be combined or combined with each other, in part or in whole, and technically various interlocking and driving are possible. Each embodiment may be implemented independently of each other or may be implemented together in an association.

Hereinafter, specific embodiments will be described with reference to the accompanying drawings.

Figure 1:
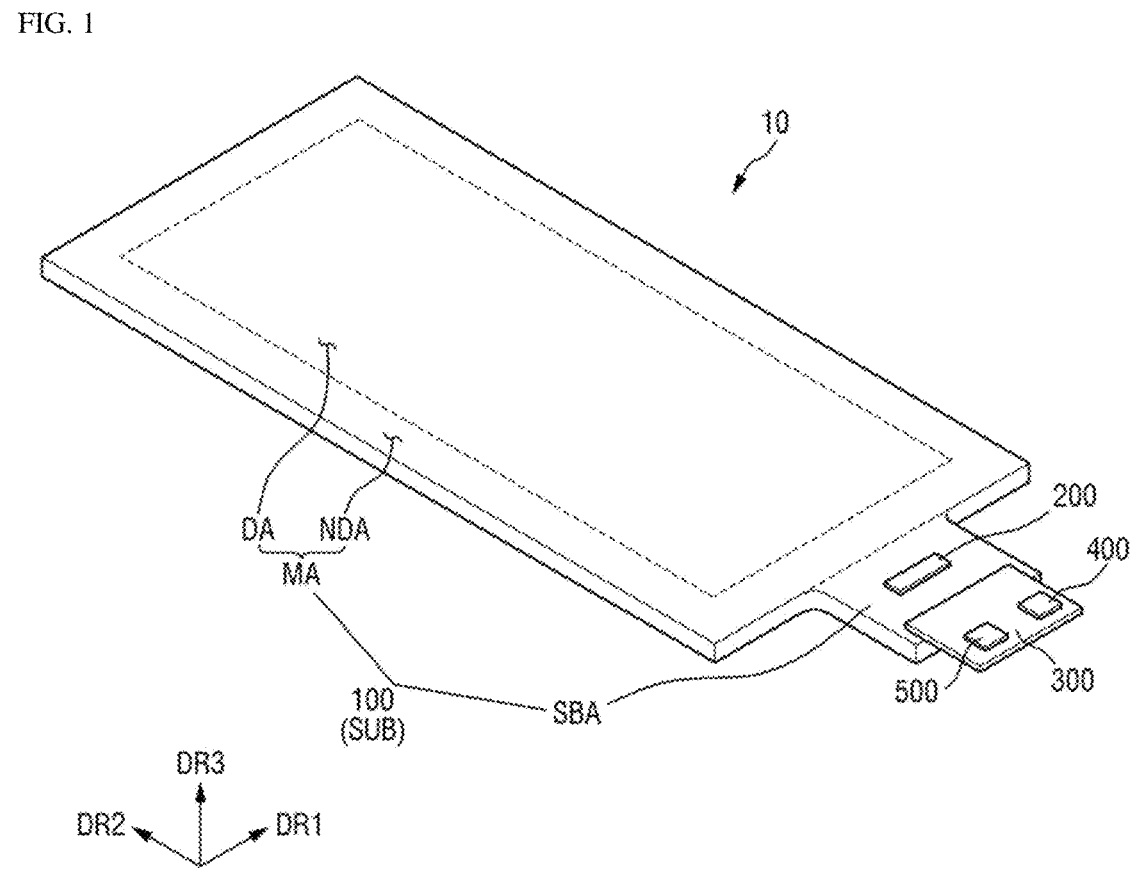
Figure 2:
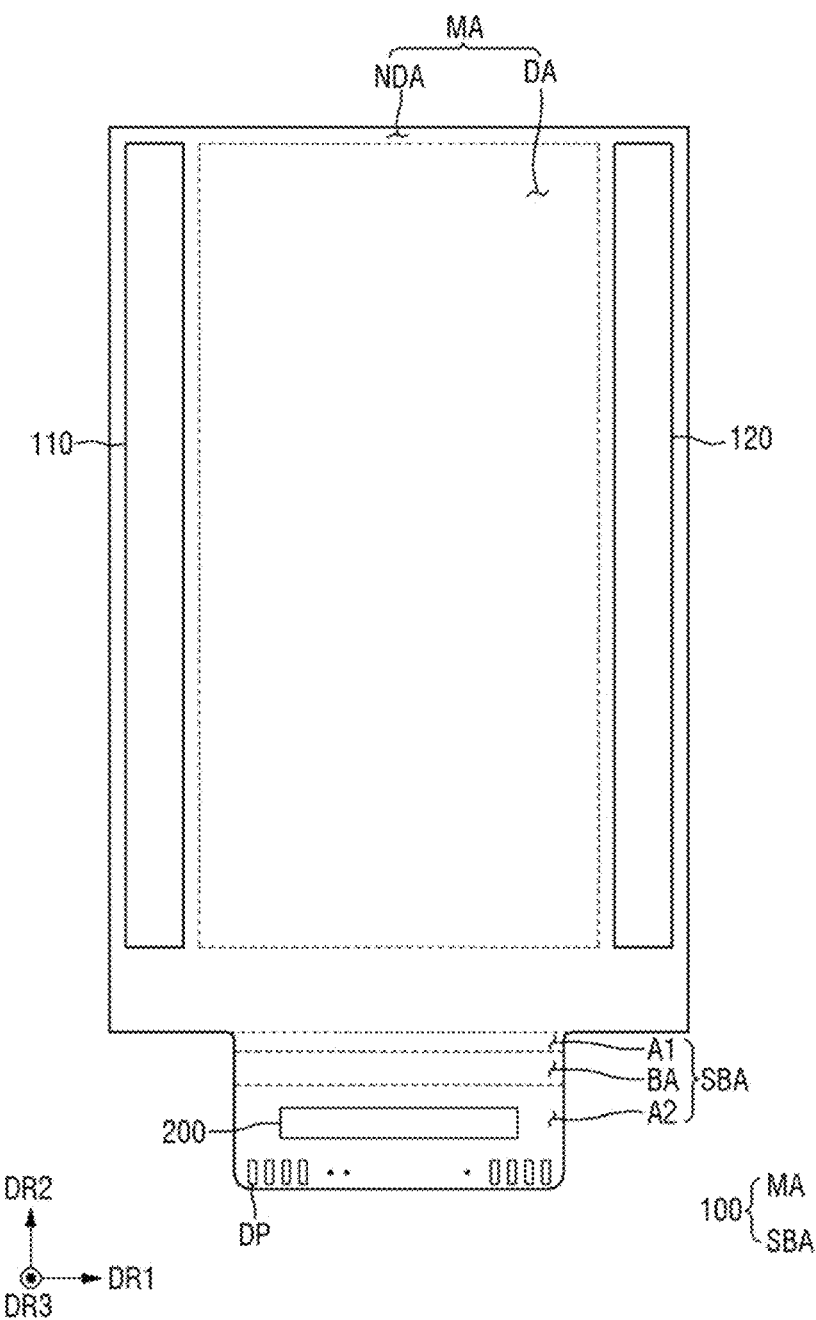
FIG. 2 is a plan view illustrating the arrangement structure of a display panel and a display driving circuit illustrated in FIG. 1.

FIG. 1 is a perspective view of a display device 10 according to an embodiment. FIG. 2 is a plan view illustrating the arrangement structure of a display panel 100 and a display driving circuit illustrated in FIG. 1.

Referring to FIGS. 1 and 2, the display device 10 according to the embodiment may be applied to portable electronic devices such as mobile phones, smartphones, tablet personal computers (PCs), mobile communication terminals, electronic notebooks, electronic books, portable multimedia players (PMPs), navigation devices, and ultra-mobile PCs (UMPCs). Alternatively, the display device 10 according to the embodiment may be applied as a display unit of a television, a laptop computer, a monitor, a billboard, or an Internet of things (IoT) device. Alternatively, the display device 10 according to the embodiment may be applied to wearable devices such as smart watches, watch phones, glass-like displays, and head-mounted displays (HMDs). Alternatively, the display device 10 according to the embodiment may be applied to a dashboard of a vehicle, a center fascia of a vehicle, a center information display (CID) disposed on a dashboard of a vehicle, or a display disposed on the back of a front seat as an entertainment for rear-seat passengers of a vehicle.

The display device 10 may be a light emitting display device such as an organic light emitting display device using an organic light emitting diode, a quantum dot light emitting display device including a quantum dot light emitting layer, an inorganic light emitting display device including an inorganic semiconductor, or a micro- or nano-light emitting display device using a micro- or nano-light emitting diode. A case where the display device 10 is an organic light emitting display device will be mainly described below, but the present disclosure is not limited thereto.

The display panel 100 may be shaped like a rectangular plane having short sides in a first direction DR1 and long sides in a second direction DR2 intersecting the first direction DR1. Each corner where a short side extending in the first direction DR1 meets a long side extending in the second direction DR2 may be right-angled or may be rounded with a predetermined curvature. The planar shape of the display panel 100 is not limited to a quadrilateral shape but may also be another polygonal shape, a circular shape, or an oval shape. The display panel 100 may be formed flat, but the present disclosure is not limited thereto. For example, the display panel 100 may include curved portions formed at left and right ends and having a constant or varying curvature. In addition, the display panel 100 may be formed to be flexible so that it can be curved, bent, folded, or rolled.

A substrate SUB of the display panel 100 may be divided into a main area MA and a sub-area SBA.

The main area MA may be divided into a display area DA displaying an image and a non-display area NDA located around the display area DA.

The non-display area NDA may neighbor the display area DA. The non-display area NDA may be an area outside the display area DA. The non-display area NDA may surround the display area DA. The non-display area NDA may be an edge area of the display panel 100. In an embodiment, no pixels are present in the non-display area NDA.

The display area DA includes display pixels for displaying an image, infrared light emitting pixels for emitting infrared light, and light sensing pixels for sensing light reflected from an object placed in front, such as a part of a user's body (e.g., a finger, the back of a hand, a wrist, scalp, facial skin, etc.), a vegetable, a fruit or a plant. For example, the object may be placed in front of the display area DA. The display pixels, the infrared light emitting pixels, and the light sensing pixels may be alternately disposed according to a preset arrangement order and may be evenly disposed throughout the display area DA. The display area DA may occupy most of the main area MA. The display area DA may be disposed in a center of the main area MA.

The sub-area SBA may include a first area A1, a second area A2, and a bending area BA.

The first area A1 is an area protruding from a side of the main area MA in the second direction DR2. A side of the first area A1 may contact the non-display area NDA of the main area MA, and the other side of the first area A1 may contact the bending area BA.

The second area A2 is an area in which pads DP and a main driving circuit 200 are disposed. The main driving circuit 200 may be attached to driving pads of the second area A2 using a conductive adhesive member such as an anisotropic conductive film. A circuit board 300 may be attached to the pads DP of the second area A2 using a conductive adhesive member. A side of the second area A2 may contact the bending area BA.

The bending area BA is an area that is bent. When the bending area BA is bent, the second area A2 may be disposed under the first area A1 and under the main area MA. The bending area BA may be disposed between the first area A1 and the second area A2. A side of the bending area BA may contact the first area A1, and the other side of the bending area BA may contact the second area A2.

Figure 3:
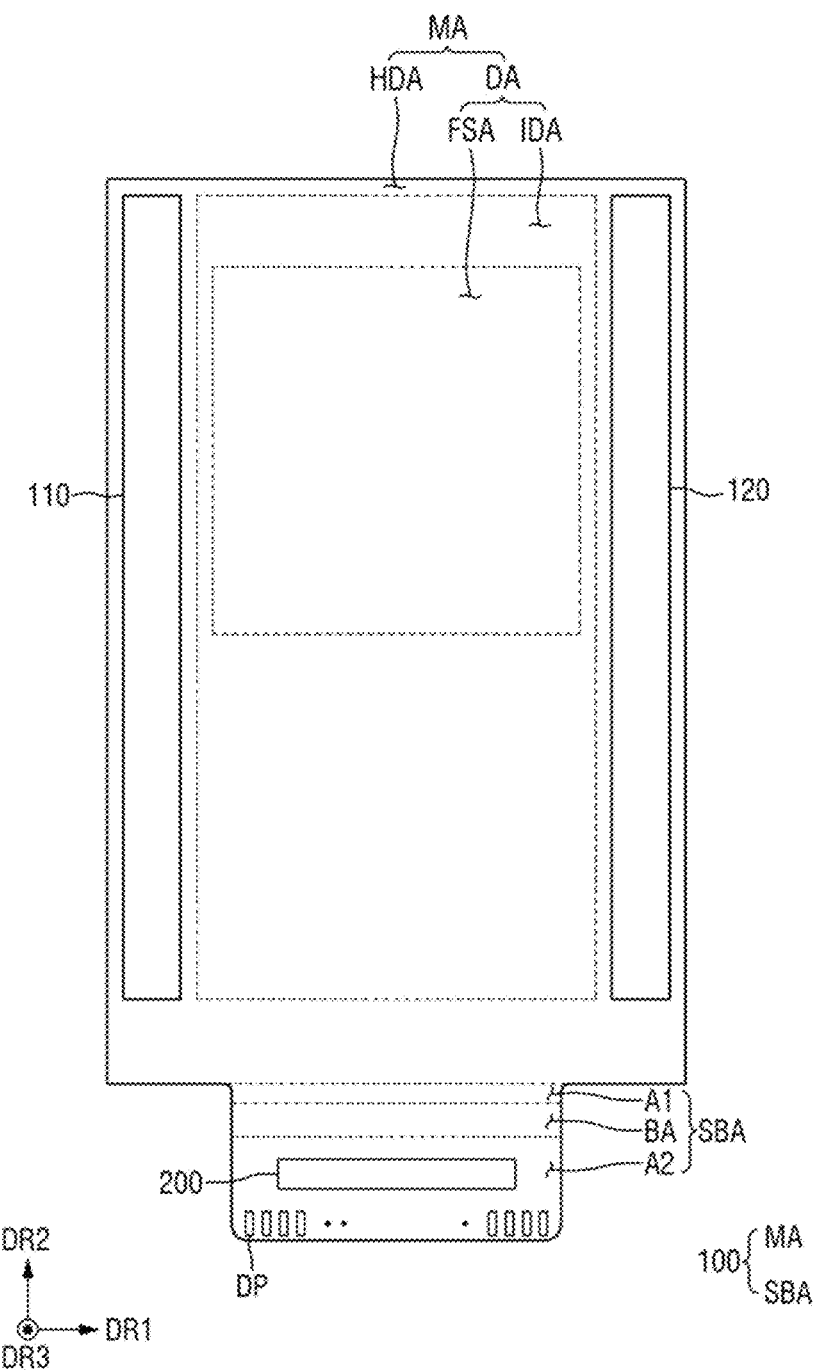
FIG. 3 is a plan view illustrating the arrangement structure of a display panel and a display driving circuit according to an embodiment.
Figure 4:
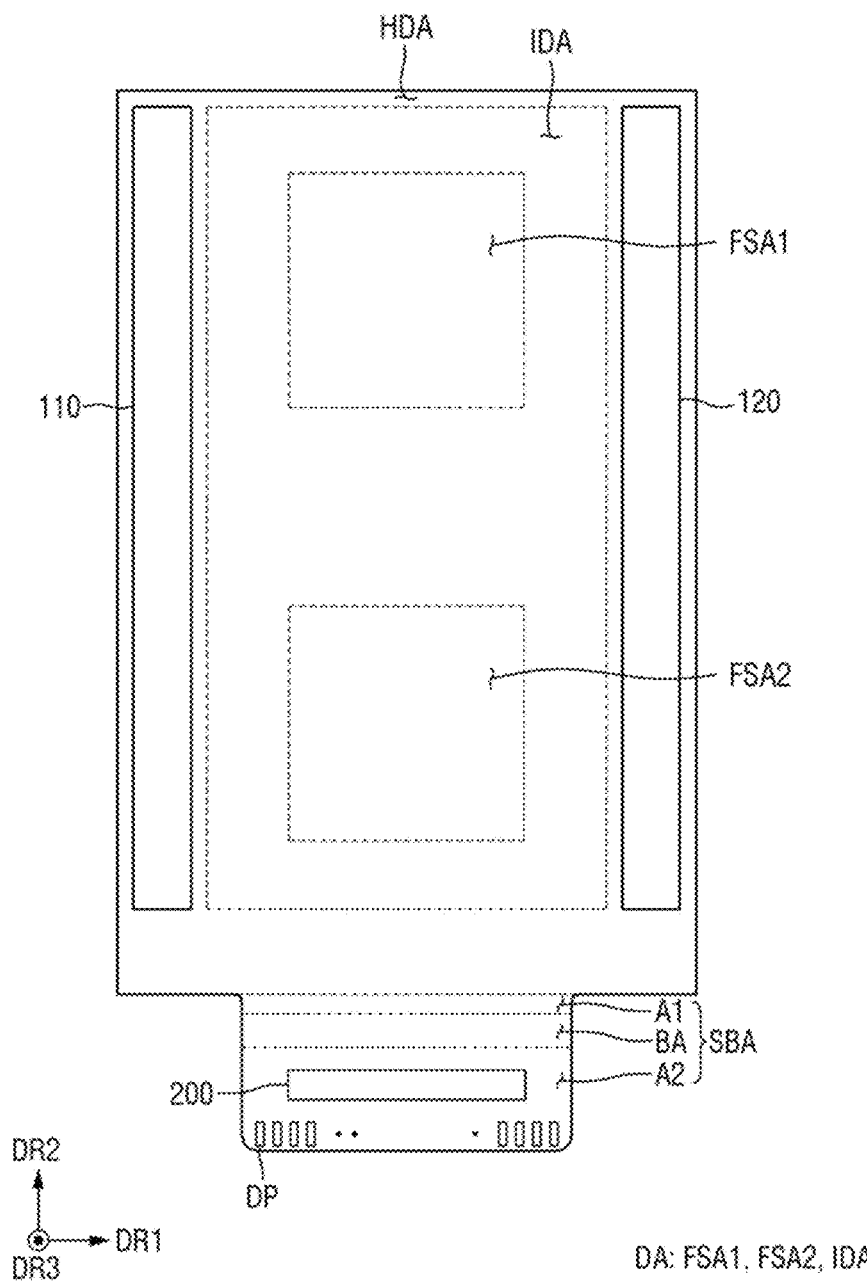
FIG. 4 is a plan view illustrating the arrangement structure of a display panel and a display driving circuit according to an embodiment.

FIG. 3 is a plan view illustrating the arrangement structure of a display panel 100 and a display driving circuit according to an embodiment. FIG. 4 is a plan view illustrating the arrangement structure of a display panel 100 and a display driving circuit according to an embodiment.

Referring to FIG. 3, a display area DA may be divided into an image display area IDA in which only display pixels are disposed without infrared light emitting pixels and light sensing pixels and a reflected light sensing area FSA in which a combination of display pixels, infrared light emitting pixels, and light sensing pixels are disposed. In other words, the infrared light emitting pixels and the light sensing pixels may be disposed together with the display pixels only in a preset reflected light sensing area FSA of the display area DA of the display panel 100.

Referring to FIG. 4, a display area DA may be divided into an image display area IDA in which only display pixels are disposed and a plurality of reflected light sensing areas FSA1 and FSA2 in which display pixels, infrared light emitting pixels and light sensing pixels are disposed. In other words, a reflected light sensing area FSA in which a combination of infrared light emitting pixels and light sensing pixels are disposed together with display pixels may be divided into a plurality of reflected light sensing areas FSA1 and FSA2, for example, first and second reflected light sensing areas FSA1 and FSA2. The first and second reflected light sensing areas FSA1 and FSA2 may be formed at different positions, that is, in different areas of the display area DA. The structure of an example in which infrared light emitting pixels and light sensing pixels are alternately disposed together with display pixels in the entire display area DA will be described below. While FIG. 4 shows two separate light sensing areas, there may be more than two light sensing areas in alternate embodiments.

Figure 5:
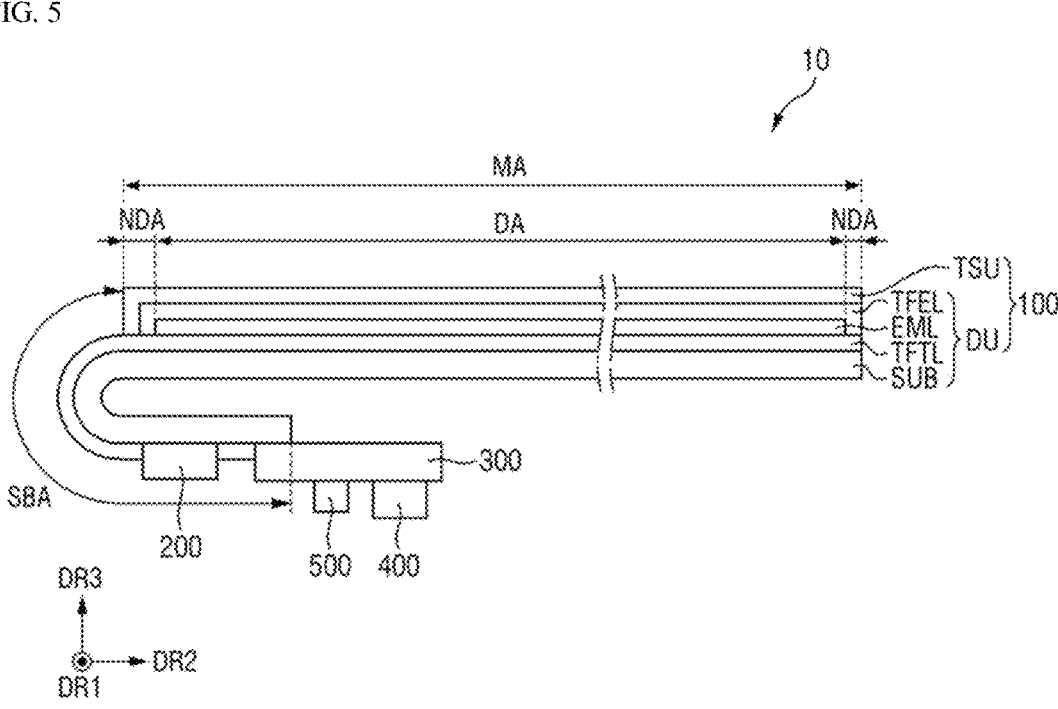
FIG. 5 is a detailed side view of the display device according to the embodiment.

FIG. 5 is a detailed side view of the display device 10 according to the embodiment.

Referring to FIGS. 4 and 5, the sub-area SBA may be bent, and in this case, may be disposed under the main area MA. The sub-area SBA may overlap the main area MA in a third direction DR3.

A length or area of the sub-area SBA in the first direction DR1 may be smaller than a length or area of the main area MA in the first direction DR1 or may be substantially equal to the length or area of the main area MA in the first direction DR1. The sub-area SBA may be bent, and in this case, may be disposed under the main area MA. The sub-area SBA may overlap the main area MA in the third direction DR3.

A touch sensing unit TSU for sensing a touch position of a body part such as a finger, a stylus pen, or an electronic pen may be disposed in a front portion of the display panel 100 including the display area DA. The touch sensing unit TSU may include a plurality of touch electrodes to sense a user's touch in a capacitive manner.

The touch sensing unit TSU includes a plurality of touch electrodes arranged to cross each other in the first and second directions DR1 and DR2. Specifically, the touch electrodes may be formed to extend in a wiring area (or a non-image display area in which wirings are formed) between display pixels so as not to overlap the display pixels, infrared light emitting pixels and light sensing pixels arranged in the display area DA. The touch electrodes may form mutual capacitance to transmit touch sensing signals, which vary according to a user's touch, to a touch sensing circuit 500.

The touch sensing circuit 500 may sense a change in mutual capacitance between the touch electrodes input from the touch electrodes, generate touch data according to the change in capacitance and coordinate data of a position where a touch has been sensed, and supply the generated data to the main driving circuit 200.

The circuit board 300 may be attached to an end of the sub-area SBA. The touch sensing circuit 500 may be mounted on the circuit board 300 and electrically connected to the touch electrodes of the touch sensing unit TSU. In addition, the circuit board 300 may be electrically connected to the display panel 100 and the main driving circuit 200.

The display panel 100 and the main driving circuit 200 may receive digital video data, timing signals, and driving voltages through the circuit board 300. The circuit board 300 may be a flexible printed circuit board, a printed circuit board, or a flexible film such as a chip on film.

The main driving circuit 200 may generate digital data and electrical control signals for driving the display panel 100. Each of a component detection circuit 400 and the touch sensing circuit 500 as well as the main driving circuit 200 may be formed as an integrated circuit. Each of the main driving circuit 200, the component detection circuit 400, and the touch sensing circuit 500 may be attached onto the display panel 100 or the circuit board 300 using a chip on glass (COG) method, a chip on plastic (COP) method, or an ultrasonic bonding method. However, the present disclosure is not limited thereto. For example, the component detection circuit 400 and the touch sensing circuit 500 as well as the main driving circuit 200 may also be attached onto the circuit board 300 using a chip on film (COF) method.

Figure 6:
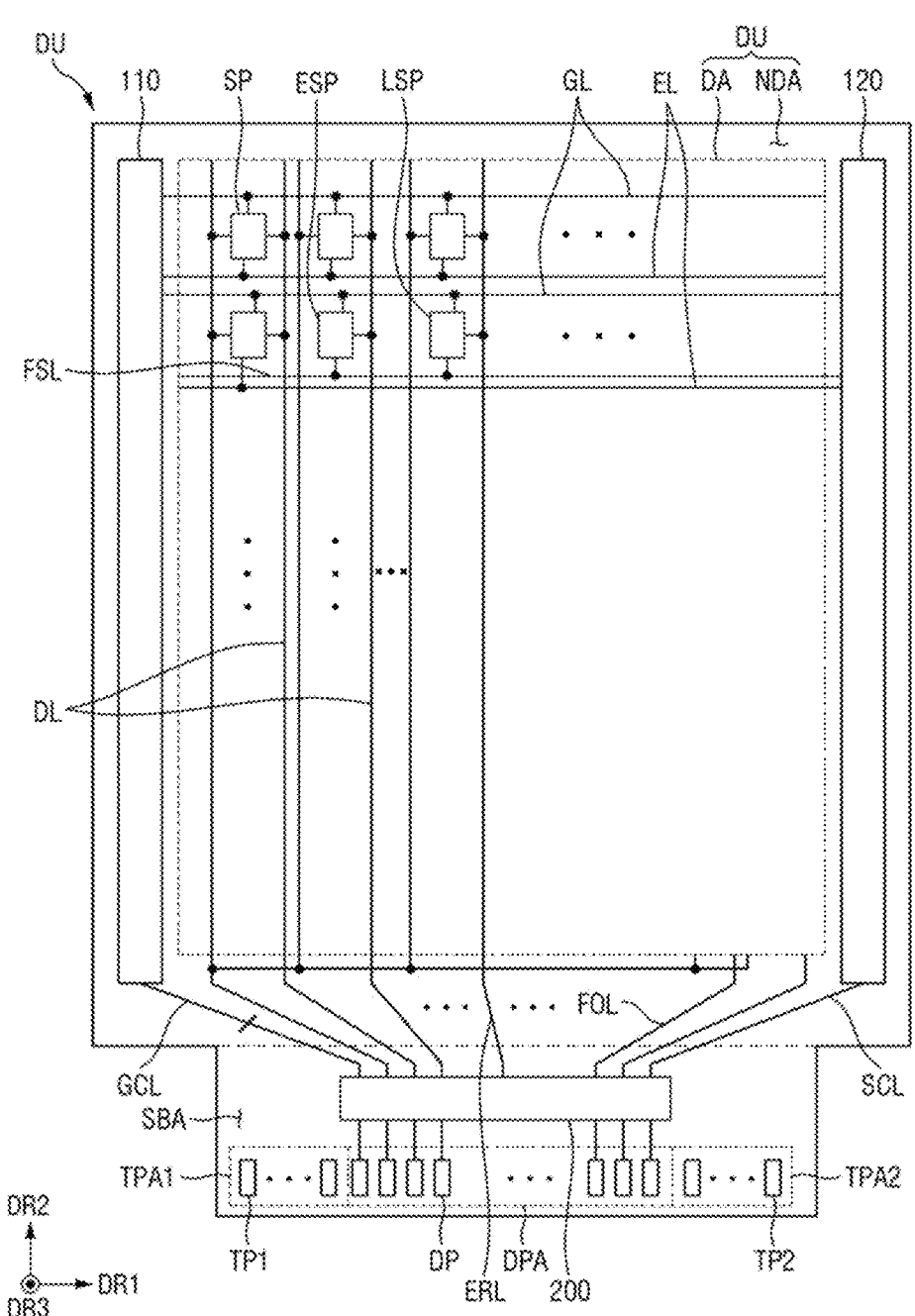
FIG. 6 is a schematic layout view of an example of the display panel illustrated in FIGS. 1 through 5.

FIG. 6 is a schematic layout view of an example of the display panel 100 illustrated in FIGS. 1 through 5. Specifically, FIG. 6 is a layout view illustrating the display area DA and the non-display area NDA of a display module DU before the touch sensing unit TSU is formed.

Referring to FIG. 6, a display scan driver 110, a light sensing scan driver 120, and the main driving circuit 200 may be disposed on the display panel 100 of the display device 10 according to the embodiment. In addition, the component detection circuit 400, the touch sensing circuit 500, and a power supply unit (not illustrated) may be disposed on the circuit board 300 connected to the display panel 100. Here, the main driving circuit 200, the component detection circuit 400, and the touch sensing circuit 500 may be integrally formed as a one-chip type and mounted on the display panel 100 or the circuit board 300. However, for ease of functional description, an example in which the main driving circuit 200, the component detection circuit 400, and the touch sensing circuit 500 are formed as different integrated circuits will be described below.

The display panel 100 may include display pixels SP, infrared light emitting pixels ESP, light sensing pixels LSP, display scan wirings GL, emission control wirings EL, data wirings DL, light sensing scan wirings FSL, and light sensing signal wirings ERL disposed in the display area DA. Each of the display scan driver 110 and the light sensing scan driver 120 may be disposed in the non-display area NDA.

The display scan wirings GL sequentially supply display scan signals received from the display scan driver 110 in units of horizontal lines to a plurality of display pixels SP for each horizontal line. In addition, the display scan signals may be supplied to the infrared light emitting pixels ESP through the display scan wirings GL. The display scan wirings GL may extend in the first direction DR1 and may be spaced apart from each other in the second direction DR2 intersecting the first direction DR1.

The emission control wirings EL sequentially supply emission control signals received from the display scan driver 110 in units of horizontal lines to a plurality of display pixels SP for each horizontal line. In addition, the emission control signals may be supplied to the infrared light emitting pixels ESP through the emission control wirings EL. The emission control wirings EL may extend in the first direction DR1 in parallel with the display scan wirings GL and may be spaced apart from each other in the second direction DR2 intersecting the first direction DR1.

The data wirings DL may supply data voltages received from the main driving circuit 200 to the display pixels SP and the infrared light emitting pixels ESP. The data wirings DL may extend in the second direction DR2 and may be spaced apart from each other in the first direction DR1.

The light sensing scan wirings FSL sequentially supply sensing scan signals received from the light sensing scan driver 120 in units of horizontal lines to the light sensing pixels LSP. The light sensing scan wirings FSL may extend in the first direction DR1 and may be spaced apart from each other in the second direction DR2 intersecting the first direction DR1.

The light sensing signal wirings ERL are connected between the light sensing pixels LSP and the component detection circuit 400 to supply light sensing signals output from the light sensing pixels LSP to the component detection circuit 400. The light sensing signal wirings ERL may lie and extend in the second direction DR2 according to the placement direction of the component detection circuit 400 and may be spaced apart from each other in the first direction DR1.

The non-display area NDA may surround the display area DA. The display scan driver 110, the light sensing scan driver 120, fan-out wirings FOL, display control wirings GCL, and light sensing control wirings SCL may be disposed in the non-display area NDA.

The display pixels SP displaying an image, the infrared light emitting pixels ESP emitting infrared light, and the light sensing pixels LSP sensing reflected light incident from a front side may be arranged in a matrix in the first direction DR1 and the second direction DR2. For example, the reflected light may be light reflected from an objected located in front of the display area DA. For example, the display pixels SP, the infrared light emitting pixels ESP, and the light sensing pixels LSP may be arranged in a horizontal stripe structure along the first direction DR1 or may be arranged in a vertical stripe structure along the second direction DR2.

The display scan driver 110 may be disposed in the non-display area NDA. Although the display scan driver 110 is disposed on a side (e.g., a left side) of the display panel 100 in the drawing, the present disclosure is not limited thereto. For example, the display scan driver 110 may also be disposed on both sides (e.g., left and right sides) of the display panel 100.

The display scan driver 110 may be electrically connected to the main driving circuit 200 through the display control wirings GCL. The display scan driver 110 receives a scan control signal from the main driving circuit 200, sequentially generates display scan signals in units of horizontal line driving periods according to the scan control signal, and sequentially supplies the display scan signals to the display scan wirings GL. In addition, the display scan driver 110 may sequentially generate emission control signals according to the scan control signal from the main driving circuit 200 and sequentially supply the emission control signals to the emission control wirings EL.

The display control wirings GCL may extend from the main driving circuit 200 to the display scan driver 110 according to the placement position of the display scan driver 110. The display control wirings GCL may supply a scan control signal received from the main driving circuit 200 to the display scan driver 110.

The light sensing scan driver 120 may be disposed in a different part of the non-display area NDA from the display scan driver 110. Although the light sensing scan driver 120 is disposed on the other side (e.g., the right side) of the display panel 100 in FIG. 6, the present disclosure is not limited thereto. The light sensing scan driver 120 may be electrically connected to the main driving circuit 200 through the light sensing control wirings SCL. The light sensing scan driver 120 receives a light sensing control signal from the main driving circuit 200 and sequentially generates reset control signals and sensing scan signals in units of horizontal line driving periods according to the light sensing control signal. Then, the light sensing scan driver 120 sequentially supplies the sequentially generated reset control signals to sensing reset wirings. In addition, the light sensing scan driver 120 may sequentially generate sensing scan signals according to the light sensing control signal from the main driving circuit 200 and sequentially supply the sensing scan signals to the light sensing scan wirings FSL.

The light sensing control wirings SCL may extend from the main driving circuit 200 to the light sensing scan driver 120 according to the placement position of the light sensing scan driver 120. The light sensing control wirings SCL may supply a light sensing control signal received from the main driving circuit 200 to the light sensing scan driver 120.

The main driving circuit 200 may output signals and voltages for driving the display panel 100 to the fan-out wirings FOL. The main driving circuit 200 may supply data voltages to the data wirings DL through the fan-out wirings FOL. The data voltages may be supplied to the display pixels SP and may determine luminances of the display pixels SP. The main driving circuit 200 may supply a scan control signal to the display scan driver 110 through the display control wirings GCL.

The main driving circuit 200 may generate digital video data according to biomarker information analyzed by the component detection circuit 400 or may execute an application program that presents the biomarker information (e.g., in text or graphic form). For example, the biomarker information may be determined by the component detection circuit 400. For example, the main driving circuit 200 may execute an application program or a preset program and present the biomarker information in text or graphic form according to the graphic form and type of the program.

In an embodiment, the component detection circuit 400 modulates light sensing signals of the light sensing pixels LSP received through the light sensing signal wirings ERL into digital light sensing signals. Then, the component detection circuit 400 generates and stores biomarker information by analyzing the digital light sensing signals using a preset component analysis algorithm or component analysis program. The biomarker information may be transmitted to and shared with the main driving circuit 200.

Figure 7:
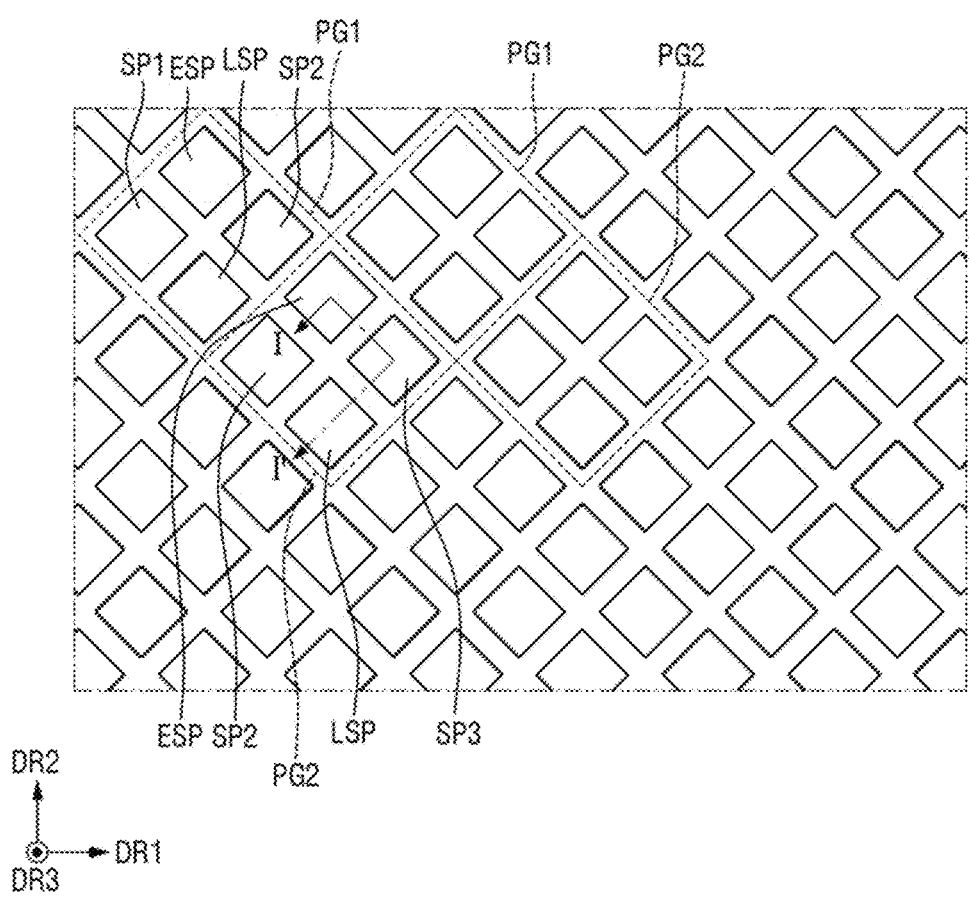
FIG. 7 is a layout view illustrating the arrangement structure of display pixels, infrared light emitting pixels, and light sensing pixels in a light sensing area according to an embodiment.

FIG. 7 is a layout view illustrating the arrangement structure of display pixels SP, infrared light emitting pixels ESP, and light sensing pixels LSP in a reflected light sensing area FAS according to an embodiment.

Referring to FIG. 7, in the display area DA or the reflected light sensing area FAS of the display area DA according to the embodiment, two display pixels, i.e., first and second display pixels SP1 and SP2 respectively displaying red light and green light, one infrared light emitting pixel ESP, and one light sensing pixel LSP may be arranged to form a first unit pixel PG1. In addition, two display pixels, i.e., second and third display pixels SP2 and SP3 respectively displaying green light and blue light, one infrared light emitting pixel ESP, and one light sensing pixel LSP may be arranged to form a second unit pixel PG2. The first and second unit pixels PG1 and PG2 may be arranged in a quad structure or a Pentile™ matrix structure.

For example, the first and second unit pixels PG1 and PG2 may alternately be arranged in a zigzag pattern along the first direction DR1 and the second direction DR2. In addition, the first and second unit pixels PG1 and PG2 may be alternately arranged in a matrix along the first direction DR1 and the second direction DR2. Alternatively, the first and second unit pixels PG1 and PG2 may be alternately arranged in a Pentile™ matrix along the first direction DR1 and the second direction DR2.

Figure 8:
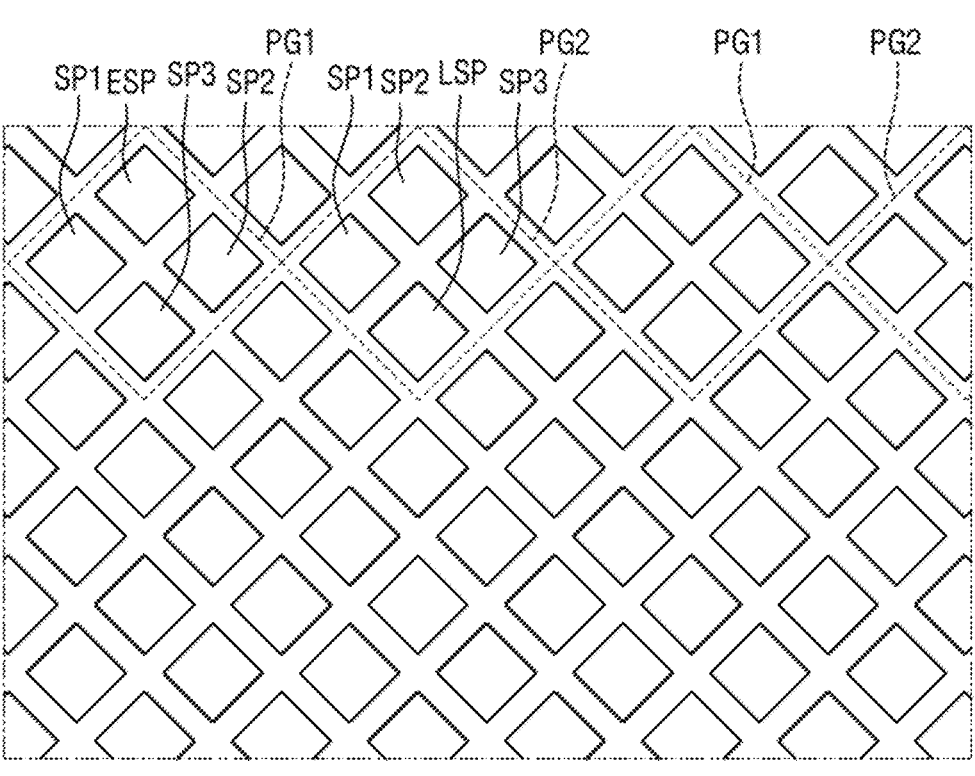
FIG. 8 is a layout view illustrating the arrangement structure of display pixels, infrared light emitting pixels, and light sensing pixels according to an embodiment.
Figure 8:

FIG. 8 is a layout view illustrating the arrangement structure of display pixels SP, infrared light emitting pixels ESP, and light sensing pixels LSP in a reflected light sensing area FAS according to an embodiment.

Referring to FIG. 8, in the display area DA or the reflected light sensing area FAS of the display area DA according to the embodiment, three display pixels, i.e., first through third display pixels SP1 through SP3 respectively displaying red light, green light and blue light and one infrared light emitting pixel ESP are arranged to form each first unit pixel PG1. In addition, three display pixels, i.e., first through third display pixels SP1 through SP3 respectively displaying red light, green light and blue light and one light sensing pixel LSP are arranged to form each second unit pixel PG2. Accordingly, the first and second unit pixels PG1 and PG2 may be alternately arranged in a matrix along the first direction DR1 and the second direction DR2. The first and second unit pixels PG1 and PG2 may be arranged in a quad structure or a Pentile™ matrix structure.

For example, the first and second unit pixels PG1 and PG2 may be alternately arranged in the form of vertical or horizontal stripes along the first direction DR1 and the second direction DR2. In addition, the first and second unit pixels PG1 and PG2 may be alternately arranged in a zigzag pattern along the first direction DR1 and the second direction DR2. Alternatively, the first and second unit pixels PG1 and PG2 may be alternately arranged in a Pentile™ matrix along the first direction DR1 and the second direction DR2.

As another example, three display pixels SP1 through SP3 respectively displaying red light, green light and blue light, one infrared light emitting pixel ESP, and one light sensing pixel LSP may form each unit pixel and may be arranged along the first direction DR1 and the second direction DR2.

Each of the red, green and blue display pixels SP1 through SP3 and the infrared light emitting pixels ESP may be connected to any one of the display scan wirings GL and any one of the emission control wirings EL.

Each of the display pixels SP1 through SP3 may receive a data voltage of a data wiring DL according to a display scan signal of a display scan wiring GL and an emission control signal of an emission control wiring EL and may emit light by supplying a driving current to a light emitting element according to the data voltage. Each of the infrared light emitting pixels ESP may also receive a data voltage of a data wiring DL according to a display scan signal and an emission control signal and may emit light by supplying a driving current to a light emitting element according to the data voltage. The data voltage applied to each of the infrared light emitting pixels ESP may be the same voltage as the data voltage applied to each of the blue third display pixels SP3.

Each of the light sensing pixels LSP may be connected to one of the light sensing scan wirings FSL and one of the light sensing signal wirings ERL. Each of the light sensing pixels LSP may generate a light sensing signal corresponding to the amount of reflected light incident from the front side and transmit the light sensing signal to a light sensing signal wiring ERL in response to a sensing scan signal from a light sensing scan wiring FSL.

Figure 9:
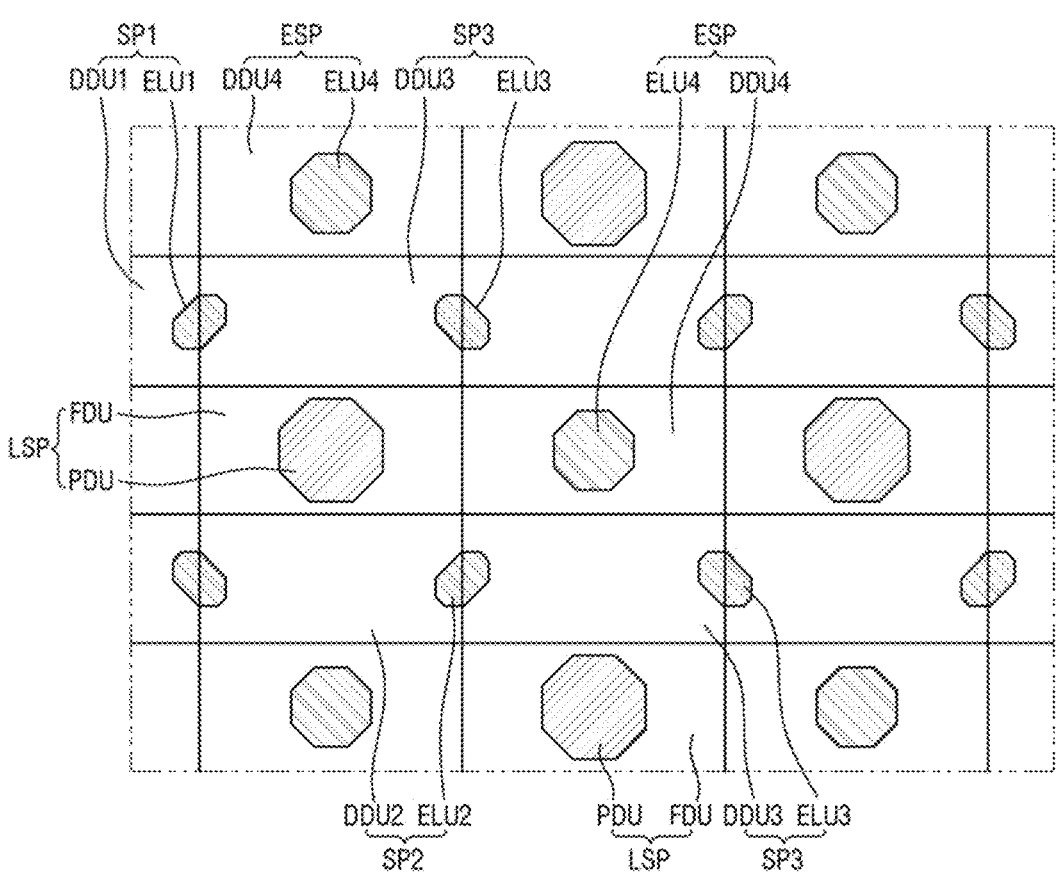
FIG. 9 is a detailed layout view of an area where display pixels, infrared light emitting pixels, and light sensing pixels are arranged according to an embodiment.

FIG. 9 is a detailed layout view of an area where display pixels SP, infrared light emitting pixels ESP, and light sensing pixels LSP are arranged according to an embodiment.

Referring to FIG. 9, a first unit pixel PG1 including first and second display pixels SP1 and SP2, an infrared light emitting pixel ESP and a light sensing pixel LSP and a second unit pixel PG2 including second and third display pixels SP2 and SP3, an infrared light emitting pixel ESP and a light sensing pixel LSP may be alternately arranged in the display area DA.

In other words, the first display pixel SP1, the second display pixel SP2, one infrared light emitting pixel ESP, and one light sensing pixel LSP may be defined as the first unit pixel PG1. In addition, the second display pixel SP2, the third display pixel SP3, one infrared light emitting pixel ESP, and one light sensing pixel LSP may be defined as the second unit pixel PG2. Each of the first and second unit pixels PG1 and PG2 may be defined as a minimum unit of subpixels that can display white while emitting infrared light or sensing reflected light incident from the front side.

The first display pixel SP1 of the first unit pixel PG1 may include a first light emitting unit ELU1 emitting first light and a first pixel driving unit DDU1 for supplying a driving current to a light emitting element of the first light emitting unit ELUL. The first light may be light of a red wavelength band. For example, a main peak wavelength of the first light may range from 600 nm to 750 nm or from approximately or about 600 nm to approximately or about 750 nm.

The second display pixel SP2 may include a second light emitting unit ELU2 emitting second light and a second pixel driving unit DDU2 for supplying a driving current to a light emitting element of the second light emitting unit ELU2. The second light may be light of a green wavelength band. For example, a main peak wavelength of the second light may range from 480 nm to 560 nm or from approximately or about 480 nm to approximately or about 560 nm.

The second display pixel SP2 may be included in each of the first and second unit pixels PG1 and PG2.

The third display pixel SP3 of the second unit pixel PG2 may include a third light emitting unit ELU3 emitting third light and a third pixel driving unit DDU3 for supplying a driving current to a light emitting element of the third light emitting unit ELU3. The third light may be light of a blue wavelength band. For example, a main peak wavelength of the third light may range from 370 nm to 460 nm or from approximately or about 370 nm to approximately or about 460 nm.

The infrared light emitting pixel ESP included in each of the first and second unit pixels PG1 and PG2 may include a fourth light emitting unit ELU4 emitting infrared light and a fourth pixel driving unit DDU4 for supplying a driving current to a light emitting element of the fourth light emitting unit ELU4. The infrared light emitted from the fourth light emitting unit ELU4 may be light in a wavelength band ranging from 750 nm to 900 nm or ranging from approximately or about 750 nm to approximately or about 900 nm. Alternatively, the fourth light emitting unit ELU4 may emit the third light in the blue wavelength band (e.g., 370 to 460 nm), like the third light emitting unit ELU3 of the third display pixel SP3. When the fourth light emitting unit ELU4 emits light in the blue wavelength band, a wavelength conversion layer may be further formed on a front surface (or upper surface) of the fourth light emitting unit ELU4 to shift the light in the blue wavelength band to light in an infrared wavelength band and output the light in the infrared wavelength band.

The light sensing pixel LSP included in each of the first and second unit pixels PG1 and PG2 includes a light sensing unit PDU sensing reflected light incident from the front side and a sensing driving unit FDU transmitting a light sensing signal from the light sensing unit PDU. The detailed structure of the infrared light emitting pixel ESP included in each of the first and second unit pixels PG1 and PG2 is the same as the detailed structure of the first through third display pixels SP1 through SP3. In an embodiment, an organic light emitting material included in the fourth light emitting unit ELU4 of the infrared light emitting pixel ESP is different from organic light emitting materials included in the first through third light emitting units ELU1 through ELU3.

As illustrated in FIG. 9, the first light emitting unit ELU1, the second light emitting unit ELU2, the third light emitting unit ELU3, the fourth light emitting unit ELU4, and the light sensing unit PDU may have an octagonal planar shape. However, the present disclosure is not limited thereto. The first light emitting unit ELU1, the second light emitting unit ELU2, the third light emitting unit ELU3, the fourth light emitting unit ELU4, and the light sensing unit PDU may also have a quadrilateral planar shape such as a rhombus or a polygonal planar shape other than a quadrilateral and an octagon.

In addition, due to the placement positions and planar shapes of the first light emitting unit ELU1, the second light emitting unit ELU2, the third light emitting unit ELU3, and the fourth light emitting unit ELU4 (or the light sensing unit PDU), a distance between a center of the first light emitting unit ELU1 and a center of the fourth light emitting unit ELU4 (or the light sensing unit PDU) neighboring each other and a distance between a center of the second light emitting unit ELU2 and the center of the fourth light emitting unit ELU4 (or the light sensing unit PDU) neighboring each other may be substantially the same.

Figure 10:
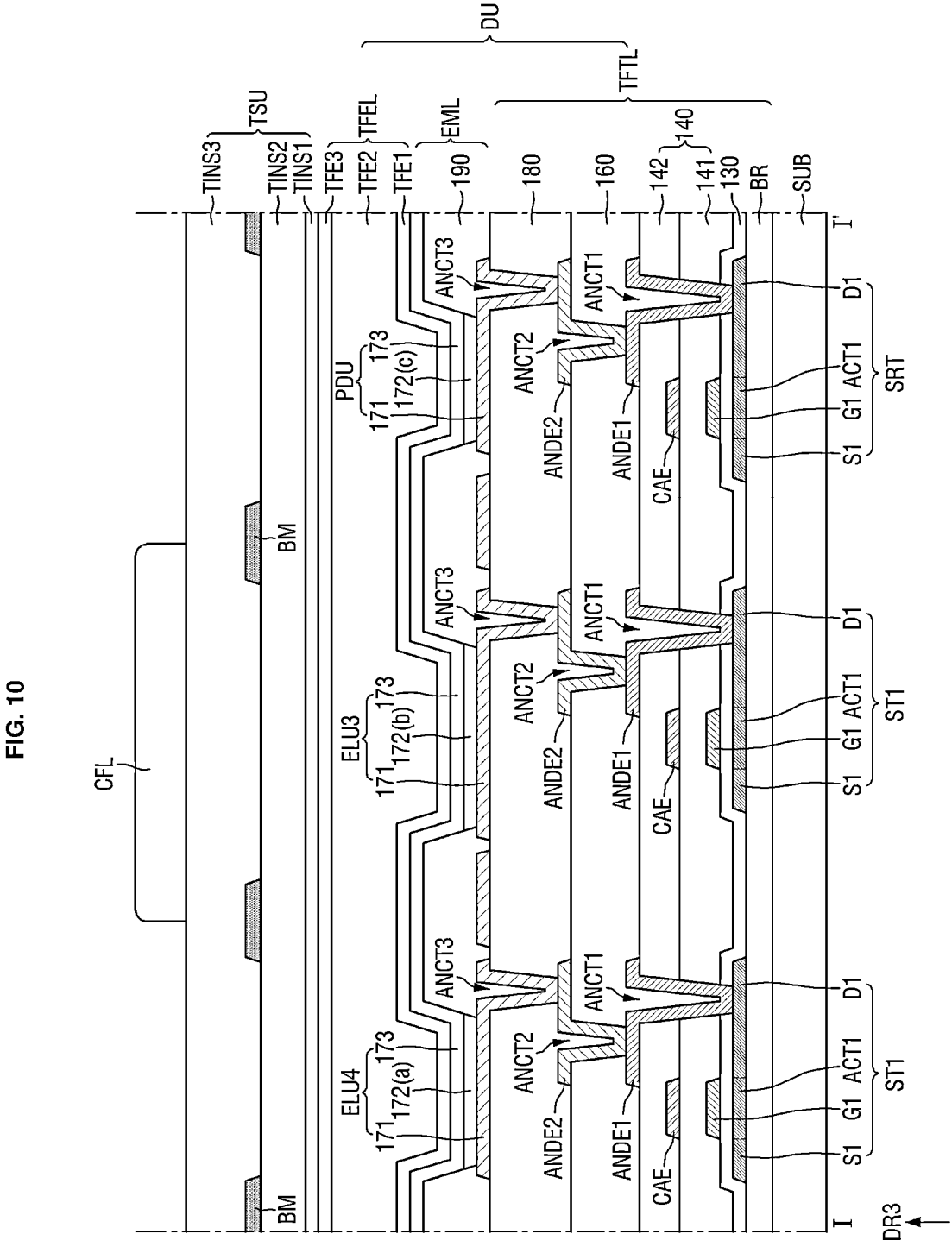
FIG. 10 is a cross-sectional view of a display area taken along line I-I' of FIG. 7.

FIG. 10 is a cross-sectional view of the display area DA taken along line I-I' of FIG. 7. Specifically, FIG. 10 is a cross-sectional view illustrating a portion of a cross section of the fourth light emitting unit ELU4 and the fourth pixel driving unit DDU4 of an infrared light emitting pixel ESP, the third light emitting unit ELU3 and the third pixel driving unit DDU3, and the light sensing unit PDU and the sensing driving unit FDU.

Referring to FIG. 10, a barrier layer BR may be disposed on a substrate SUB. The substrate SUB may be made of an insulating material such as polymer resin. For example, the substrate SUB may be made of polyimide. The substrate SUB may be a flexible substrate that can be bent, folded, rolled, or the like.

The barrier layer BR is a layer for protecting transistors of a thin-film transistor layer TFTL and light emitting layers 172 of a light emitting element layer EML from moisture introduced through the substrate SUB which is vulnerable to moisture penetration. The barrier layer BR may be composed of a plurality of inorganic layers stacked alternately. For example, the barrier layer BR may be a multilayer in which one or more inorganic layers selected from a silicon nitride layer, a silicon oxynitride layer, a silicon oxide layer, a titanium oxide layer, and an aluminum oxide layer are alternately stacked.

Thin-film transistors ST1 of pixel driving units and sensing transistors SRT of sensing driving units FDU may be disposed on the barrier layer BR. Each of the thin-film transistors ST1 and the sensing transistors SRT includes an active layer ACT1, a gate electrode G1, a source electrode S1, and a drain electrode D1.

For example, the active layers ACT1, the source electrodes S1, and the drain electrodes D1 of the thin-film transistors ST1 may be disposed on the barrier layer BR. The active layers ACT1 of the thin-film transistors ST1 include polycrystalline silicon, monocrystalline silicon, low-temperature polycrystalline silicon, amorphous silicon, or an oxide semiconductor. The active layers ACT1 overlapping the gate electrodes G1 in the third direction DR3 which is a thickness direction of the substrate SUB may be defined as channel regions. The source electrodes S1 and the drain electrodes D1 are regions not overlapping the gate electrodes G1 in the third direction DR3 and may be formed to have conductivity by doping a silicon semiconductor or an oxide semiconductor with ions or impurities.

A gate insulating layer 130 may be disposed on the active layers ACT1, the source electrodes S1, and the drain electrodes D1 of the thin-film transistors ST1 and the sensing transistors SRT. The gate insulating layer 130 may be an inorganic layer, for example, a silicon nitride layer, a silicon oxynitride layer, a silicon oxide layer, a titanium oxide layer, or an aluminum oxide layer.

The gate electrodes G1 of the thin-film transistors ST1 may be disposed on the gate insulating layer 130. The gate electrodes G1 may overlap the active layers ACT1 in the third direction DR3. Each of the gate electrodes G1 may be a single layer or a multilayer made of any one or more selected from molybdenum (Mo), aluminum (Al), chromium (Cr), gold (Au), titanium (Ti), nickel (Ni), neodymium (Nd), copper (Cu), and alloys thereof.

A first interlayer insulating layer 141 may be disposed on the gate electrodes G1 of the thin-film transistors ST1 and the sensing transistors SRT. The first interlayer insulating layer 141 may be an inorganic layer, for example, a silicon nitride layer, a silicon oxynitride layer, a silicon oxide layer, a titanium oxide layer, or an aluminum oxide layer. The first interlayer insulating layer 141 may be composed of a plurality of inorganic layers.

Capacitor electrodes CAE may be disposed on the first interlayer insulating layer 141. The capacitor electrodes CAE may overlap the gate electrodes G1 of the first thin-film transistors ST1 in the third direction DR3. Since the first interlayer insulating layer 141 has a predetermined dielectric constant, capacitors may be formed by the capacitor electrodes CAE, the gate electrodes G1, and the first interlayer insulating layer 141 disposed between the capacitor electrodes CAE and the gate electrodes G1. Each of the capacitor electrodes CAE may be a single layer or a multilayer made of any one or more selected from molybdenum (Mo), aluminum (Al), chromium (Cr), gold (Au), titanium (Ti), nickel (Ni), neodymium (Nd), copper (Cu), and alloys thereof.

A second interlayer insulating layer 142 may be disposed on the capacitor electrodes CAE. The second interlayer insulating layer 142 may be an inorganic layer, for example, a silicon nitride layer, a silicon oxynitride layer, a silicon oxide layer, a titanium oxide layer, or an aluminum oxide layer. The second interlayer insulating layer 142 may be composed of a plurality of inorganic layers.

First anode connection electrodes ANDE1 may be disposed on the second interlayer insulating layer 142. The first anode connection electrodes ANDE1 may be connected to the drain electrodes D1 of the thin-film transistors ST1 through first connection contact holes ANCT1 penetrating the gate insulating layer 130, the first interlayer insulating layer 141, and the second interlayer insulating layer 142. Each of the first anode connection electrodes ANDE1 may be a single layer or a multilayer made of any one or more selected from molybdenum (Mo), aluminum (Al), chromium (Cr), gold (Au), titanium (Ti), nickel (Ni), neodymium (Nd), copper (Cu), and alloys thereof.

A first planarization layer 160 may be disposed on the first anode connection electrodes ANDE1 to flatten steps formed by the thin-film transistors ST1. The first planarization layer 160 may be made of an organic layer such as acryl resin, epoxy resin, phenolic resin, polyamide resin, or polyimide resin.

Second anode connection electrodes ANDE2 may be disposed on the first planarization layer 160. The second anode connection electrodes ANDE2 may be connected to the first anode connection electrodes ANDE1 through second connection contact holes ANCT2 penetrating the first planarization layer 160. Each of the second anode connection electrodes ANDE2 may be a single layer or a multilayer made of any one or more selected from molybdenum (Mo), aluminum (Al), chromium (Cr), gold (Au), titanium (Ti), nickel (Ni), neodymium (Nd), copper (Cu), and alloys thereof.

A second planarization layer 180 may be disposed on the second anode connection electrodes ANDE2. The second planarization layer 180 may be made of an organic layer such as acryl resin, epoxy resin, phenolic resin, polyamide resin, or polyimide resin.

First electrodes (or pixel electrodes) of the light emitting units ELU1 through ELU4 and the light sensing units PDU may be disposed on the second planarization layer 180. Each of the first through third light emitting units ELU1 through ELU3 includes a first electrode 171, an organic light emitting layer 172(b), and a common electrode 173. fourth light emitting unit ELU4 includes a first electrode 171, an infrared light emitting layer 172(a), and the common electrode 173. In addition, each light sensing unit PDU includes a first electrode 171, an infrared sensing layer 172(c), and the common electrode 173.

The first electrodes 171 may be connected to the second anode connection electrodes ANDE2 through third connection contact holes ANCT3 penetrating the second planarization layer 180. The first electrodes 171 may be made of a metal material having high reflectivity, such as a stacked structure (Ti/Al/Ti) of aluminum and titanium, a stacked structure (ITO/Al/ITO) of aluminum and indium tin oxide, an APC alloy, or a stacked structure (ITO/APC/ITO) of an APC alloy and indium tin oxide. The APC alloy is an alloy of silver (Ag), palladium (Pd), and copper (Cu).

A pixel defining layer 190 may be formed on the second planarization layer 180 to cover all of the first electrodes 171.

The pixel defining layer 190 is formed on the second planarization layer 180 to separate the first electrodes 171 in order to define the first through fourth light emitting units ELU1 through ELU4 and the light sensing units PDU. Here, the pixel defining layer 190 may also cover edges of the first electrodes 171. The pixel defining layer 190 may be made of a transparent organic layer to minimize the effect on infrared light reflectance. The pixel defining layer 190 may be made of an organic layer such as photosensitive polyimide resin, polyamide resin, a black pixel defining layer (PDL), or polyimide resin through which infrared light is transmitted.

The organic light emitting layer 172(b) may be formed on each of the first electrodes 171 of the first through third light emitting units ELU1 through ELU3. The organic light emitting layer 172(b) may include an organic material to emit light of a predetermined color. For example, the organic light emitting layer 172(b) includes a hole transporting layer, an organic material layer, and an electron transporting layer.

The infrared light emitting layer 172(a) may be formed on the first electrode 171 of fourth light emitting unit ELU4. The infrared light emitting layer 172(a) may include at least one organic material selected from a low molecular weight boron-dipyrromethene derivative (BODIPY-Ph), acetone including a low molecular weight boron-dipyrromethene derivative (BODIPY-Ph), hydrocarbon (e.g., rubrene), N,N'-Di(naphthalen-1-yl)-N,N'-diphenyl-benzidine (NPB), and tris-8-hydroxyquinoline aluminum (Alq3).

The infrared sensing layer 172(c) of each light sensing unit PDU is a PIN semiconductor layer. The PIN semiconductor layer may include a P-type semiconductor layer connected to the first electrode 171, an N-type semiconductor layer connected to the common electrode 173, and an I-type semiconductor layer disposed between the P-type semiconductor layer and the N-type semiconductor layer. In this case, the I-type semiconductor layer is depleted by the P-type semiconductor layer and the N-type semiconductor layer to generate an electric field in the I-type semiconductor layer, and holes and electrons generated by light are drifted by the electric field. Accordingly, the holes may be collected to the anode through the P-type semiconductor layer, and the electrons may be collected to the cathode through the N-type semiconductor layer.

The common electrode 173 may be made of a transparent conductive material (TCO) capable of transmitting light, such as indium tin oxide (ITO) or indium zinc oxide (IZO), or a semi-transmissive conductive material such as magnesium (Mg), silver (Ag) or an alloy of Mg and Ag. When the common electrode 173 is made of a semi-transmissive conductive material, light output efficiency may be increased by a microcavity.

An encapsulation layer TFEL may be disposed on the common electrode 173. The encapsulation layer TFEL includes at least one inorganic layer to prevent oxygen or moisture from permeating into the first through fourth light emitting units ELU1 through ELU4 and the light sensing units PDU. In addition, the encapsulation layer TFEL includes at least one organic layer to protect the light emitting element layer EML from foreign substances such as dust. For example, the encapsulation layer TFE1 includes a first encapsulating inorganic layer TFE1, an encapsulating organic layer TFE2, and a second encapsulating inorganic layer TFE3.

The first encapsulating inorganic layer TFE1 may be disposed on the common electrode 173, the encapsulating organic layer TFE2 may be disposed on the first encapsulating inorganic layer TFE1, and the second encapsulating inorganic layer TFE3 may be disposed on the encapsulating organic layer TFE2. Each of the first encapsulating inorganic layer TFE1 and the second encapsulating inorganic layer TFE3 may be a multilayer in which one or more inorganic layers selected from a silicon nitride layer, a silicon oxynitride layer, a silicon oxide layer, a titanium oxide layer, and an aluminum oxide layer are alternately stacked. The encapsulating organic layer TFE2 may be an organic layer such as acryl resin, epoxy resin, phenolic resin, polyamide resin, or polyimide resin.

A touch sensing unit TSU may be mounted and disposed on the encapsulation layer TFEL including the black matrix BM.

A black matrix BM may be formed on the one insulating layer among the first to third touch insulating layers (TINS1 to TINS3) to separate areas in which the first through fourth light emitting units ELU1 through ELU4 and the light sensing units PDU are formed and to block light.

Since the fourth light emitting units ELU4 of the infrared light emitting pixels ESP emit light in an infrared wavelength band, in an embodiment, the front surfaces (or the upper surfaces) of the fourth light emitting units ELU4 are formed to be transparent. In addition, since the light sensing units PDU operate on reflected light, front surfaces (or upper surfaces) of the light sensing units PDU may also be formed to be transparent. That is, there is no need to form openings or color filters CFL4 on the front surfaces of the fourth light emitting units ELU4 and the light sensing units PDU.

Figure 11:
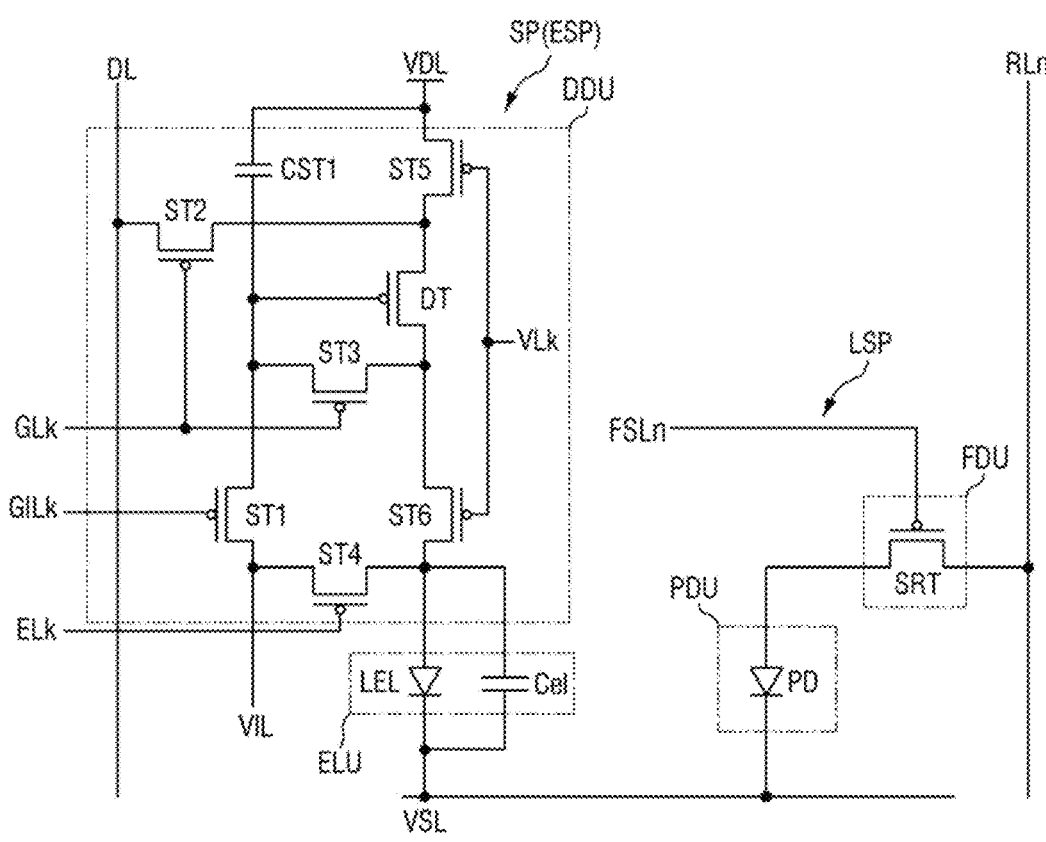
FIG. 11 is a circuit diagram of a display pixel, an infrared light emitting pixel, and a light sensing pixel according to an embodiment.

FIG. 11 is a circuit diagram of a display pixel SP, an infrared light emitting pixel ESP, and a light sensing pixel LSP according to an embodiment.

Referring to FIG. 11, each of the display pixel SP and the infrared light emitting pixel ESP according to the embodiment may be connected to a kl display initialization wiring GILk, a kl display write wiring GWLk, and a k$^{th}$ display control wiring GCLk. In addition, each of the display pixel SP and the infrared light emitting pixel ESP may be connected to a first driving voltage wiring VDL to which a first driving voltage is supplied, a second driving voltage wiring VSL to which a second driving voltage is supplied, and a third driving voltage wiring VIL to which a third driving voltage is supplied. Alphabet letters k and n used in place of numbers below are positive integers or natural numbers excluding 0.

The display pixel SP and the infrared light emitting pixel ESP may be formed in the same circuit structure. In particular, the infrared light emitting pixel ESP may be formed in the same circuit structure as a blue display pixel SP. The circuit structure of one display pixel SP will be described below as an example.

As described above, each display pixel SP may include a light emitting unit ELU and a pixel driving unit DDU. The light emitting unit ELU may include a light emitting element LEL defined as a light emitting layer. The pixel driving unit DDU may include a driving transistor DT, switch elements, and a capacitor CST1. The switch elements include first through sixth transistors ST1 through ST6.

The driving transistor DT may include a gate electrode, a first electrode, and a second electrode. The driving transistor DT controls a drain-source current Ids (hereinafter, referred to as a "driving current") flowing between the first electrode and the second electrode according to a data voltage applied to the gate electrode. In an embodiment, the driving current Ids flowing through a channel of the driving transistor DT is proportional to the square of a difference between a voltage Vsg between the first electrode and the gate electrode of the driving transistor DT and a threshold voltage as shown in Equation 1.

$$Ids = k' \times (Vsg - Vth)^2, \qquad \text{(Equation 1)}$$

where k' is a proportional coefficient determined by the structure and physical characteristics of the driving transistor DT, Vsg is a voltage between the first electrode and the gate electrode of the driving transistor DT, and Vth is a threshold voltage of the driving transistor DT.

The light emitting element LEL emits light according to the driving current Ids. As the driving current Ids increases, the amount of light emitted from the light emitting element LEL may increase.

The light emitting element LEL may be an organic light emitting diode including an organic light emitting layer disposed between an anode and a cathode. Alternatively, the light emitting element LEL may be an inorganic light emitting element including an inorganic semiconductor disposed between an anode and a cathode. Alternatively, the light emitting element LEL may be a quantum dot light emitting element including a quantum dot light emitting layer disposed between an anode and a cathode. Alternatively, the light emitting element LEL may be a micro-light emitting element including a micro-light emitting diode disposed between an anode and a cathode.

The anode of the light emitting element LEL may be connected to a first electrode of the fourth transistor ST4 and a second electrode of the sixth transistor ST6, and the cathode of the light emitting element LEL may be connected to the second driving voltage wiring VSL. A parasitic capacitance Cel may be formed between the anode and the cathode of the light emitting element LEL.

The first transistor ST1 is turned on by an initialization scan signal of the kl display initialization wiring GILk to connect the gate electrode of the driving transistor DT to the third driving voltage wiring VIL. Therefore, the third driving voltage of the third driving voltage wiring VIL may be applied to the gate electrode of the driving transistor DT. The first transistor ST1 may have a gate electrode connected to the kl display initialization wiring GILk, a first electrode connected to the gate electrode of the driving transistor DT, and a second electrode connected to the third driving voltage wiring VIL.

The second transistor ST2 is turned on by a display scan signal of the $k^{th}$ display write wiring GLk to connect the first electrode of the driving transistor DT to an $n^{th}$ data wiring DL. Therefore, a data voltage of the $n^{th}$ data wiring DL may be applied to the first electrode of the driving transistor DT. The second transistor ST2 may have a gate electrode connected to the $k^{th}$ display write wiring GLk, a first electrode connected to the first electrode of the driving transistor DT, and a second electrode connected to the $n^{th}$ data wiring DL.

The third transistor ST3 is turned on by the display scan signal of the kl display write wiring GLk to connect the gate electrode and the second electrode of the driving transistor DT. When the gate electrode and the second electrode of the driving transistor DT are connected, the driving transistor DT operates as a diode. The third transistor ST3 may have a gate electrode connected to the kl display write wiring GLk, a first electrode connected to the second electrode of the driving transistor DT, and a second electrode connected to the gate electrode of the driving transistor DT.

The fourth transistor ST4 is turned on by a display control signal of the kl display control wiring ELk to connect the anode of the light emitting element LEL to the third driving voltage wiring VIL. The third driving voltage of the third driving voltage wiring VIL may be applied to the anode of the light emitting element LEL. The fourth transistor ST4 has a gate electrode connected to the kl display control wiring GCLk, the first electrode connected to the anode of the light emitting element LEL, and a second electrode connected to the third driving voltage wiring VIL.

The fifth transistor ST5 is turned on by a control signal of a kl emission control wiring VLk to connect the first electrode of the driving transistor DT to the first driving voltage wiring VDL. The fifth transistor ST5 has a gate electrode connected to the $k^{th}$ emission control wiring ELk, a first electrode connected to the first driving voltage wiring VDL, and a second electrode connected to the first electrode of the driving transistor DT.

The sixth transistor ST6 is disposed between the second electrode of the driving transistor DT and the anode of the light emitting element LEL. The sixth transistor ST6 is turned on by the emission control signal of the $k^{th}$ emission control wiring ELk to connect the second electrode of the driving transistor DT to the anode of the light emitting element LEL. The sixth transistor ST6 has a gate electrode connected to the kl emission control wiring ELk, a first electrode connected to the second electrode of the driving transistor DT, and the second electrode connected to the anode of the light emitting element LEL.

When both the fifth transistor ST5 and the sixth transistor ST6 are turned on, the driving current Ids of the driving transistor DT according to the data voltage applied to the gate electrode of the driving transistor DT may flow to the light emitting element LEL.

The capacitor CST1 is formed between the gate electrode of the driving transistor DT and the first driving voltage wiring VDL. A first capacitor electrode of the capacitor CST1 may be connected to the gate electrode of the driving transistor DT, and a second capacitor electrode of the capacitor CST1 may be connected to the first driving voltage wiring VDL.

When the first electrode of each of the first through sixth transistors ST1 through ST6 and the driving transistor DT is a source electrode, the second electrode may be a drain electrode. Alternatively, when the first electrode of each of the first through sixth transistors ST1 through ST6 and the driving transistor DT is a drain electrode, the second electrode may be a source electrode.

An active layer of each of the first through sixth transistors ST1 through ST6 and the driving transistor DT may be made of any one of polysilicon, amorphous silicon, and an oxide semiconductor. Although a case where the first through sixth transistors ST1 through ST6 and the driving transistor DT are formed as P-type metal oxide semiconductor field effect transistors (MOSFETs) has been mainly described in FIG. 11, the present disclosure is not limited thereto. For example, the first through sixth transistors ST1 through ST6 and the driving transistor DT may also be formed as N-type MOSFETs. Alternatively, at least one of the first through sixth transistors ST1 through ST6 may be formed as an N-type MOSFET.

The light sensing pixel LSP according to the embodiment may be connected to an $n^{th}$ light sensing scan wiring FSLn and an $n^{th}$ light sensing wiring RLn.

The light sensing pixel LSP may include a light sensing unit PDU and a sensing driving unit FDU. The light sensing unit PDU may include a light sensing element PD. The sensing driving unit FDU may include a sensing transistor SRT.

The voltage of a sensing anode of the light sensing element PD may vary according to light incident on the light sensing element PD. For example, as the amount of light incident on the light sensing element PD increases, the voltage of the sensing anode of the light sensing element PD may increase.

The light sensing element PD may be a photodiode including a first electrode 171, a PIN semiconductor layer, and a common electrode 173. The first electrode 171 of the light sensing element PD may be connected to a source electrode of the sensing transistor SRT, and the common electrode 173 of the light sensing element PD may be connected to the second driving voltage wiring VSL. The PIN semiconductor layer of the light sensing element PD may include a P-type semiconductor layer connected to the first electrode 171, an N-type semiconductor layer connected to the common electrode 173, and an I-type semiconductor layer disposed between the P-type semiconductor layer and the N-type semiconductor layer. In this case, the I-type semiconductor layer is depleted by the P-type semiconductor layer (PL) and the N-type semiconductor layer (NL) to generate an electric field in the I-type semiconductor layer, and holes and electrons generated by light are drifted by the electric field. Accordingly, the holes may be collected to the first electrode 171 through the P-type semiconductor layer, and the electrons may be collected to the common electrode 173 through the N-type semiconductor layer.

The sensing transistor SRT is turned on by a sensing scan signal of the $n^{th}$ light sensing scan wiring FSLn to connect the first electrode 171 of the light sensing element PD to the $n^{th}$ light sensing wiring RLn. Therefore, the voltage of the first electrode 171 of the light sensing element PD may be applied to the $n^{th}$ light sensing wiring RLn. The sensing transistor SRT may have a gate electrode connected to the $n^{th}$ light sensing scan wiring FSLn, the source electrode connected to the sensing anode of the light sensing element PD, and a drain electrode connected to the $n^{th}$ light sensing wiring RLn.

Figure 12:
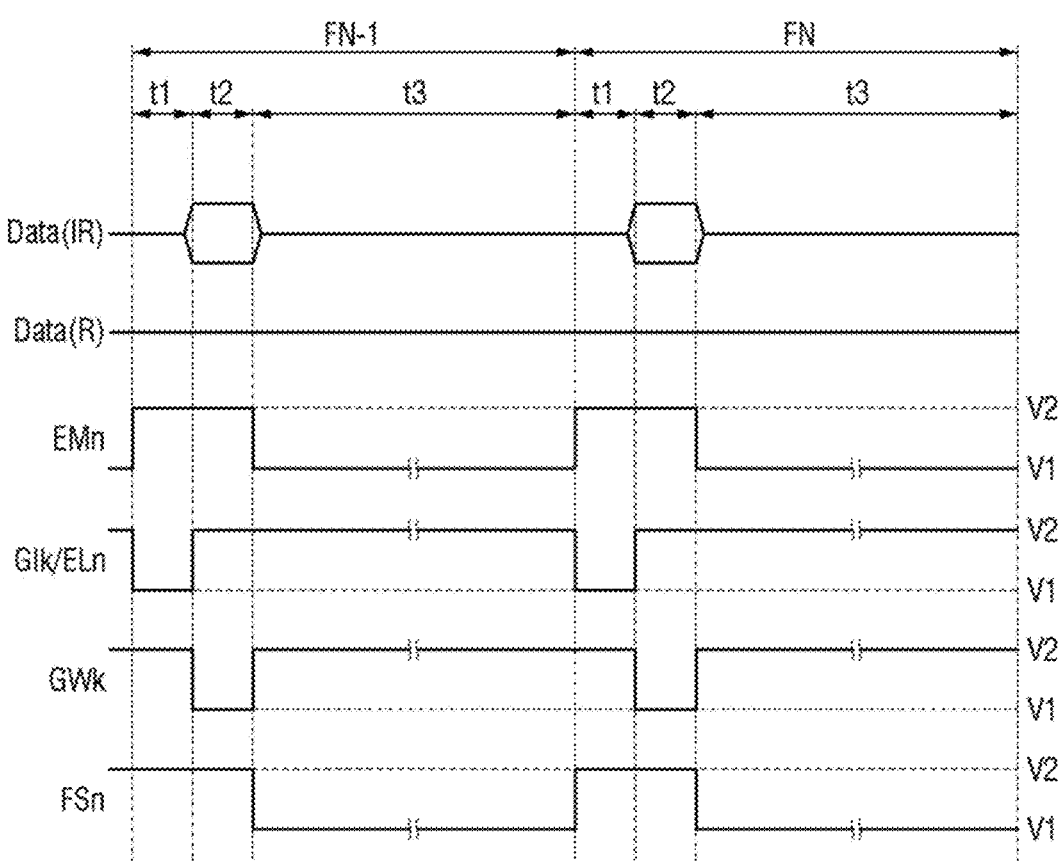
FIG. 12 is a waveform diagram of scan signals input to any one display pixel and a light sensing pixel according to an embodiment.

FIG. 12 is a waveform diagram of scan signals input to any one display pixel SP and a light sensing pixel LSP according to an embodiment.

Since a display pixel SP and an infrared light emitting pixel ESP are formed in the same circuit structure, the same scan signals supplied to the display pixel SP may also be supplied to the infrared light emitting pixel ESP.

In FIG. 12, an $n^{th}$ emission signal EMn transmitted to the $k^{th}$ emission control wiring ELk during an $(N-1)^{th}$ frame period FN-1 and an $N^{th}$ frame period FN, a $k^{th}$ display initialization signal GIk transmitted to the $k^{th}$ display initialization wiring GILk, an $n^{th}$ display control signal ELn transmitted to the $k^{th}$ display control wiring GCLk, a $k^{th}$ display scan signal GWk transmitted to the $k^{th}$ display write wiring GWLk, and an $n^{th}$ sensing scan signal FSn transmitted to the $n^{th}$ light sensing scan wiring FSLn are illustrated.

The $k^{th}$ display initialization signal GIk is a signal for controlling turning on-off of the first transistor ST1 of the display pixel SP. The $n^{th}$ display control signal ELn is a signal for controlling turning on-off of the fourth transistor ST4 of the display pixel SP. The $k^{th}$ display scan signal GWk is a signal for controlling turning on-off of the second transistor ST2 and the third transistor ST3. The $n^{th}$ emission signal EMn is a signal for controlling turning on-off of the fifth transistor ST5 and the sixth transistor ST6. The $n^{th}$ sensing scan signal FSn is a signal for controlling turning on-off of the sensing transistor SRT.

Each of the $(N-1)^{th}$ frame period FN-1 and the $N^{th}$ frame period FN may include a first period t1, a second period t2, and a third period t3.

The first period t1 is a period in which the gate electrode of the driving transistor DT is initialized to the third driving voltage, the second period t2 is a period in which a data voltage Data(IR) or Data(R) is supplied to the gate electrode of the driving transistor DT and the threshold voltage of the driving transistor DT is sampled, and the third period t3 is a period in which the light emitting element LEL emits light according to a gate voltage of the driving transistor DT. In addition, the first period t1 and the third period t3 are periods in which the light sensing element PD is exposed to light, and the second period t2 is a period in which an anode voltage of the light sensing element PD is sensed.

The $n^{th}$ emission signal EMn has a first-level voltage V1 during the third period t3 and a second-level voltage V2 during the first period t1 and the second period t2. The $k^{th}$ display scan signal GWk has the first-level voltage V1 during the second period t2 and the second-level voltage V2 during the first period t1 and the third period t3.

The $k^{th}$ display initialization signal GIk and the $n^{th}$ display control signal ELn have the first-level voltage V1 during the first period t1 and the second-level voltage V2 during the second period t2 and the third period t3. That is, the $k^{th}$ display initialization signal GIk and the $n^{th}$ display control signal ELn may be substantially the same.

The $n^{th}$ sensing scan signal FSn has the second-level voltage V2 during the first and second periods t1 and t2 and the first-level voltage V1 during the third period t3. The $n^{th}$ sensing scan signal FSn may be substantially the same as the $n^{th}$ emission signal EMn.

Each of the first period t1 and the second period t2 may be one horizontal period. One horizontal period refers to a period in which the data voltage Data(IR) or Data(R) is supplied to each of the display pixels SP disposed in one horizontal line of the display panel 100. Therefore, one horizontal period may be defined as one horizontal line scan period. The display pixels SP arranged in one horizontal line may be defined as subpixels connected to one display initialization wiring, one display write wiring, one display control wiring, and one emission control wiring.

The first-level voltage V1 may be a turn-on voltage that can turn on the first through sixth transistors ST1 through ST6 and the sensing transistor SRT. The second-level voltage V2 may be a turn-off voltage that can turn off the first through sixth transistors ST1 through ST6 and the sensing transistor SRT. The second-level voltage V2 may have a higher level than the first-level voltage V1.

The operation of the display pixel SP during the first period t1, the second period t2, and the third period t3 will now be described with reference to FIGS. 11 and 12.

First, in the first period t1, the kl display initialization signal GIk having the first-level voltage V1 is supplied to the kl display initialization wiring GILk, and the $n^{th}$ display control signal ELn having the first-level voltage V1 is supplied to the kl display control wiring GCLk.

During the first period t1, the first transistor ST1 is turned on by the kl display initialization signal GIk having the first-level voltage V1. Due to the turn-on of the first transistor ST1, the third driving voltage of the third driving voltage wiring VIL is applied to the gate electrode of the driving transistor DT. When the third driving voltage is applied to the gate electrode of the driving transistor DT during the first period t1, the voltage Vsg between the first electrode and the gate electrode of the driving transistor DT is greater than the threshold voltage Vth of the driving transistor DT. Accordingly, the driving transistor DT may be turned on. That is, since an on-bias can be applied to the driving transistor DT, hysteresis characteristics of the driving transistor DT can be improved.

In addition, during the first period t1, the fourth transistor ST4 is turned on by the $n^{th}$ display control signal ELn having the first-level voltage V1. Therefore, due to the turn-on of the fourth transistor ST4 during the first period t1, the anode of the light emitting element LEL may be initialized to the third driving voltage of the third driving voltage wiring VIL.

Second, the $k^{th}$ display scan signal GWk having the first-level voltage V1 is supplied to the $k^{th}$ display write wiring GLk during the second period t2. Therefore, during the second period t2, each of the second transistor ST2 and the third transistor ST3 is turned on by the $k^{th}$ display scan signal GWk having the first-level voltage V1.

Due to the turn-on of the third transistor ST3 during the second period t2, the gate electrode and the second electrode of the driving transistor DT are connected to each other, and the driving transistor DT operates as a diode. In addition, due to the turn-on of the second transistor ST2 during the second period t2, a data voltage Data(IR) or Vdata is supplied to the first electrode of the driving transistor DT. In this case, since the voltage (Vsg=Vdata-V1NT) between the first electrode and the gate electrode of the driving transistor DT is smaller than the threshold voltage Vth, the driving transistor DT forms a current path until the voltage Vsg between the first electrode and the gate electrode reaches the threshold voltage Vth.

Accordingly, during the second period t2, the gate electrode and the second electrode of the driving transistor DT rise to a difference voltage (Vdata-Vth) between the data voltage Vdata and the threshold voltage Vth of the driving transistor DT.

Third, the $n^{th}$ emission signal EMn having the first-level voltage V1 is supplied to the kl emission control wiring ELk during the third period t3. During the third period t3, each of the fifth transistor ST5 and the sixth transistor ST6 is turned on by the $n^{th}$ emission signal EMn having the first-level voltage V1.

Due to the turn-on of the fifth transistor ST5, the first electrode of the driving transistor DT is connected to the first driving voltage wiring VDL. Due to the turn-on of the sixth transistor ST6, the second electrode of the driving transistor DT is connected to the anode of the light emitting element LEL.

When the fifth transistor ST5 and the sixth transistor ST6 are turned on, the driving current Ids flowing according to the voltage of the gate electrode of the driving transistor DT may be supplied to the light emitting element LEL. The driving current Ids may be defined as in Equation 2.

$$Ids = k' \times \{VDD - (Vdata - Vth) - Vth\}^2. \qquad \text{(Equation 2)}$$

In Equation 2, k' is a proportional coefficient determined by the structure and physical characteristics of the driving transistor DT, Vth is a threshold voltage of the driving transistor DT, VDD is a first driving voltage of the first driving voltage wiring VDL, and Vdata is a data voltage. The voltage of the gate electrode of the driving transistor DT is (Vdata-Vth), and the voltage of the first electrode is VDD. Equation 2 is rearranged into Equation 3.

$$Ids = k' \times (VDD - Vdata)^2. \qquad \text{(Equation 3)}$$

Ultimately, the driving current Ids does not depend on threshold voltage Vth of the driving transistor DT as shown in Equation 3. That is, the threshold voltage Vth of the driving transistor DT may be compensated.

The operation of the light sensing pixel LSP during the first period t1, the second period t2, and the third period t3 will now be described with reference to FIGS. 11 and 12.

First, during the first period t1, the second-level voltage V2 is supplied to the $n^{th}$ light sensing scan wiring FSLn, the sensing transistor SRT is maintained in a reset state, and the light sensing element PD receives reflected light incident from the front side.

Next, during the second period t2, the second-level voltage V2 is supplied to the $n^{th}$ light sensing scan wiring FSLn, and the sensing transistor SRT is maintained in a turned-off state. During the second period t2, the light sensing element PD also receives reflected light incident from the front side. The voltage of the sensing anode of the light sensing element PD may rise according to light incident during the first period t1 and the second period t2.

Next, the $n^{th}$ sensing scan signal FSn having the first-level voltage V1 is supplied to the $n^{th}$ light sensing scan wiring FSLn during the third period t3. The sensing transistor SRT is turned on by the $n^{th}$ sensing scan signal FSn having the first-level voltage V1. Due to the turn-on of the sensing transistor SRT, the sensing anode of the light sensing element PD may be connected to the $n^{th}$ light sensing wiring RLn. Therefore, the component detection circuit 400 may sense the voltage of the sensing anode of the light sensing element PD through the $n^{th}$ light sensing wiring RLn.

As illustrated in FIG. 12, during at least one frame period, the main driving circuit 200 may supply the data voltage Data(IR) or Data(R) to display pixels or infrared light emitting pixels ESP emitting light of the same one color among the first through third display pixels SP1 through SP3 and the infrared light emitting pixels ESP.

For example, the main driving circuit 200 may supply an infrared data voltage Data(IR) to the infrared light emitting pixels ESP during a plurality of frame periods so that the infrared light emitting pixels ESP can emit infrared light during the frame periods. Then, the main driving circuit 200 may supply a red data voltage Data(R) to the red first display pixels SP1 during a plurality of next frame periods so that the red first display pixels SP1 can emit red light during the frame periods. Accordingly, only display pixels or infrared light emitting pixels ESP emitting light of the same one color among the first through third display pixels SP1 through SP3 and the infrared light emitting pixels ESP may emit light during at least one frame period.

In addition, the main driving circuit 200 may cause the $n^{th}$ sensing scan signal FSn to be supplied to the sensing driving units FDU of the light sensing pixels LSP through the light sensing scan driver 120 during a preset light sensing period, e.g., the third period t3 of each frame period.

In other words, the main driving circuit 200 may supply control signals to the light sensing scan driver 120 in units of at least one frame period so that the light sensing scan driver 120 supplies the $n^{th}$ sensing scan signal FSn to the $n^{th}$ light sensing scan wiring FSLn during a light sensing period for each horizontal line. Accordingly, light sensing signals of the light sensing pixels LSP may be output to the component detection circuit 400 during the preset light sensing period of each frame period.

Figure 13:
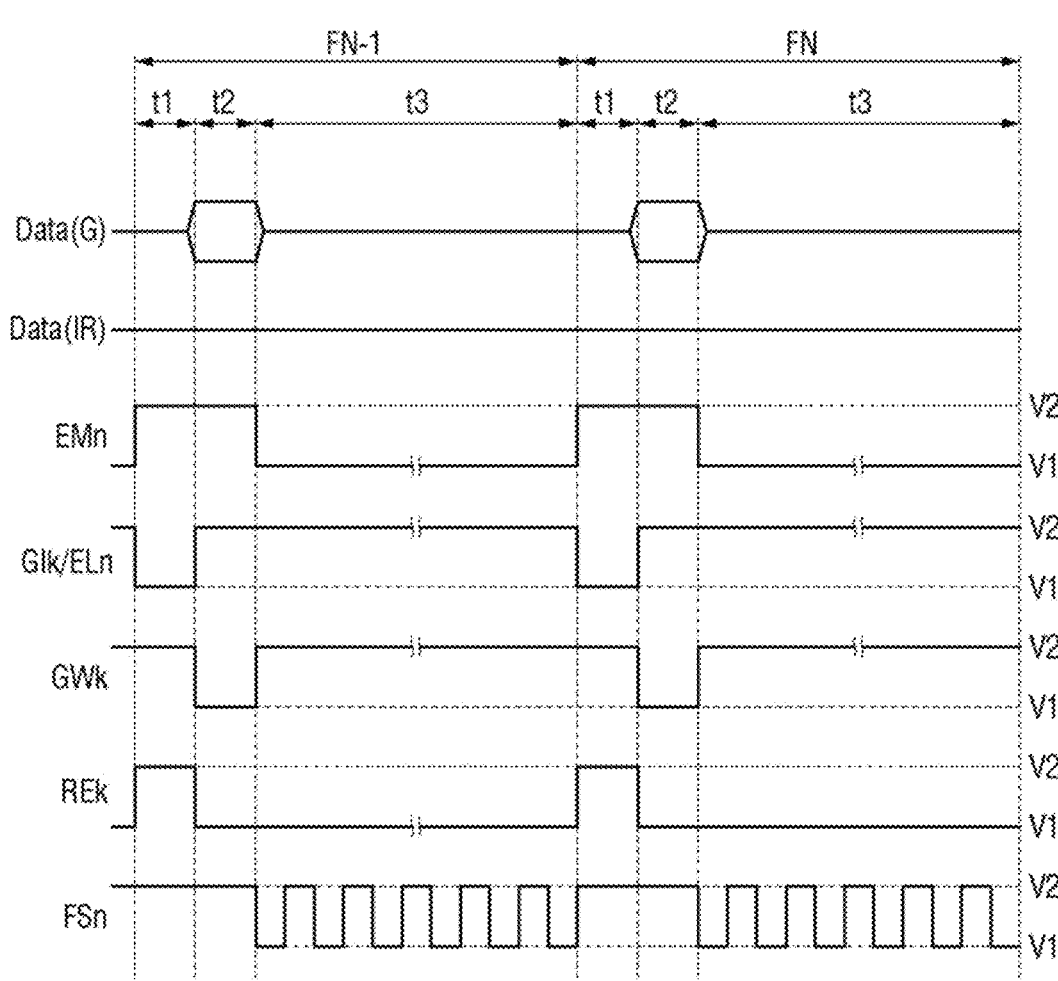
FIG. 13 is a waveform diagram of scan signals input to any one display pixel and a light sensing pixel according to an embodiment.

FIG. 13 is a waveform diagram of scan signals input to any one display pixel SP and a light sensing pixel LSP according to an embodiment.

Referring to FIG. 13, during at least one frame period, the main driving circuit 200 may supply a data voltage Data(IR) or Vdata to display pixels or infrared light emitting pixels ESP emitting light of the same one color among the first through third display pixels SP1 through SP3 and the infrared light emitting pixels ESP. That is, the main driving circuit 200 may supply a corresponding data voltage to display pixels or infrared light emitting pixels ESP emitting light of the same one color among the first through third display pixels SP1 through SP3 and the infrared light emitting pixels ESP so that only the display pixels or the infrared light emitting pixels ESP emitting light of the same one color emit light during at least one frame period.

Here, the main driving circuit 200 may cause a plurality of $n^{th}$ sensing scan signals FSn to be supplied to the sensing driving units FDU of the light sensing pixels LSP through the light sensing scan driver 120 during a preset light sensing period, e.g., a third period t3 of each frame period.

In other words, the main driving circuit 200 causes the light sensing scan driver 120 to supply an $n^{th}$ sensing scan signal FSn, which swings to a first-level voltage V1 and a second-level voltage V2, to the $n^{th}$ light sensing scan wiring FSLn during a light sensing period for each horizontal line. Accordingly, light sensing signals of the light sensing pixels LSP may be output to the component detection circuit 400 during the preset light sensing period of each frame period in response to the $n^{th}$ sensing scan signal FSn which swings to the first-level voltage V1 and the second-level voltage V2.

Figure 14:
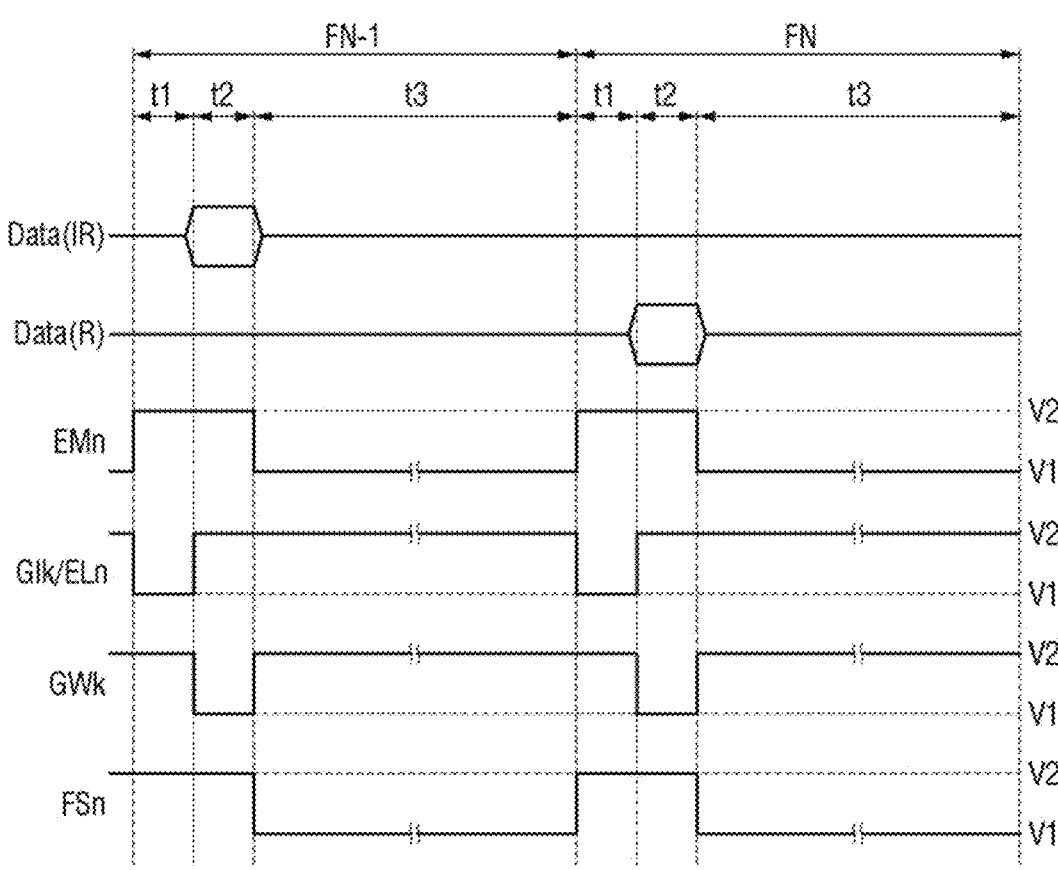
FIG. 14 is a waveform diagram of scan signals input to any one display pixel and a light sensing pixel according to an embodiment.

FIG. 14 is a waveform diagram of scan signals input to any one display pixel SP and a light sensing pixel LSP according to an embodiment.

Referring to FIG. 14, the main driving circuit 200 may sequentially supply data voltages Data(IR) and Data(R) to the first through third display pixels SP1 through SP3 and the infrared light emitting pixels ESP so that the first through third display pixels SP1 through SP3 and the infrared light emitting pixels ESP sequentially emit red, green and blue light and infrared light.

For example, the main driving circuit 200 may supply an infrared data voltage Data(IR) to the infrared light emitting pixels ESP during a first frame period so that the infrared light emitting pixels ESP emit infrared light during the first frame period. Then, the main driving circuit 200 may supply a red data voltage Data(R) to the red first display pixels SP1 during a second frame period so that the red first display pixels SP1 emit red light during the second frame period. Accordingly, the first through third display pixels SP1 through SP3 and the infrared light emitting pixels ESP may sequentially emit red, green, blue and infrared light during a plurality of frame periods.

In addition, the main driving circuit 200 may cause an $n^{th}$ sensing scan signal FSn to be supplied to the sensing driving units FDU of the light sensing pixels LSP through the light sensing scan driver 120 during a preset light sensing period, e.g., a third period t3 of each frame period. In other words, the main driving circuit 200 may cause the light sensing scan driver 120 to supply the $n^{th}$ sensing scan signal FSn to the $n^{th}$ light sensing scan wiring FSLn during a light sensing period for each horizontal line. Accordingly, light sensing signals of the light sensing pixels LSP may be output to the component detection circuit 400 during the preset light sensing period of each frame period.

Figure 15:
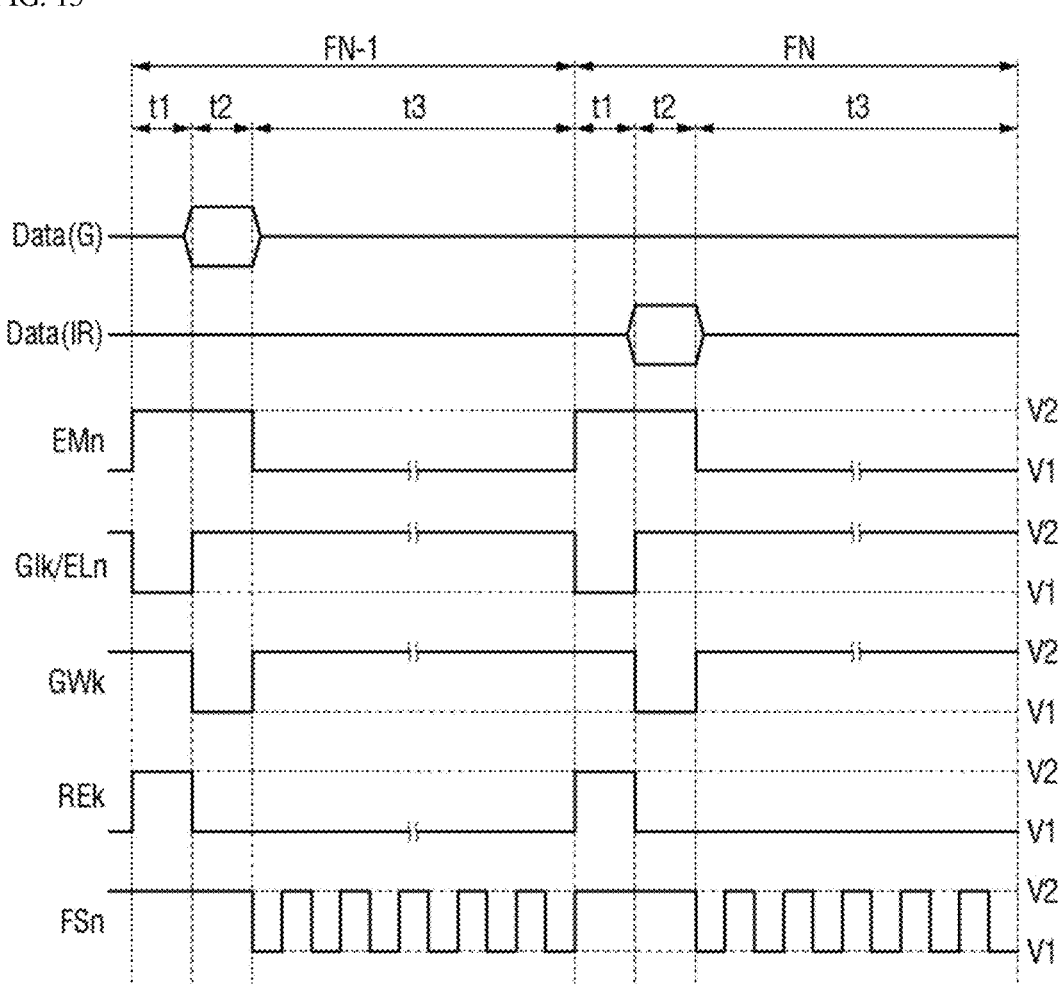
FIG. 15 is a waveform diagram of scan signals input to any one display pixel and a light sensing pixel according to an embodiment.

FIG. 15 is a waveform diagram of scan signals input to any one display pixel SP and a light sensing pixel LSP according to an embodiment.

Referring to FIG. 15, the main driving circuit 200 may sequentially supply data voltages Data(IR) and Vdata to the first through third display pixels SP1 through SP3 and the infrared light emitting pixels ESP so that the first through third display pixels SP1 through SP3 and the infrared light emitting pixels ESP sequentially emit red, green and blue light and infrared light.

Accordingly, the first through third display pixels SP1 through SP3 and the infrared light emitting pixels ESP may sequentially emit red, green, blue and infrared light during a plurality of frame periods.

Here, the main driving circuit 200 may cause a plurality of $n^{th}$ sensing scan signals FSn to be supplied to the sensing driving units FDU of the light sensing pixels LSP through the light sensing scan driver 120 during each frame period. In other words, the main driving circuit 200 causes the light sensing scan driver 120 to supply an $n^{th}$ sensing scan signal FSn, which swings to a first-level voltage V1 and a second-level voltage V2, to the $n^{th}$ light sensing scan wiring FSLn for each horizontal line. Accordingly, light sensing signals of the light sensing pixels LSP may be output to the component detection circuit 400 in response to the $n^{th}$ sensing scan signal FSn which swings to the first-level voltage V1 and the second-level voltage V2.

Figure 16:
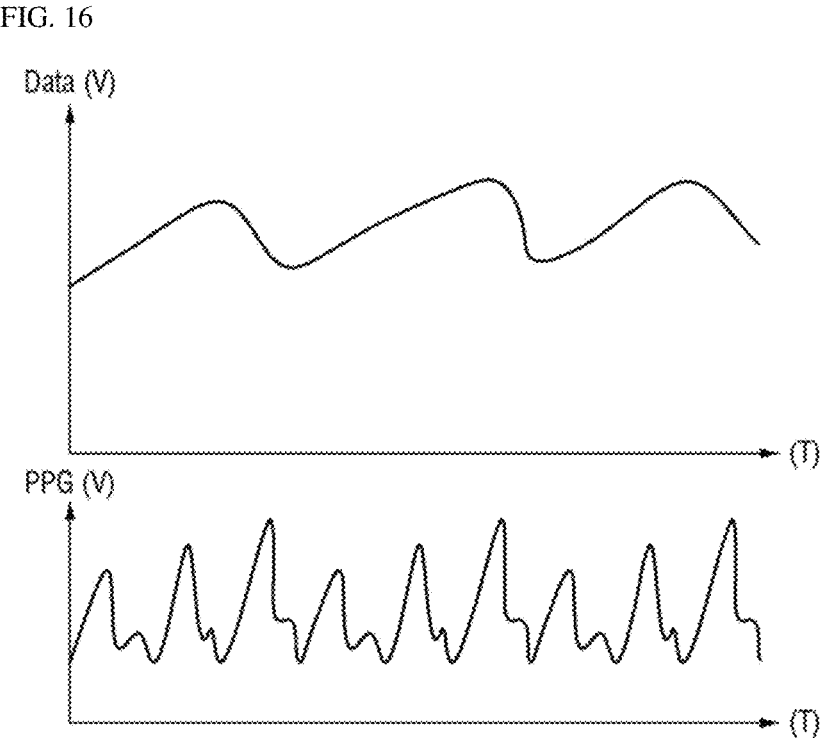
FIG. 16 is a waveform diagram illustrating a change in luminous intensity and a change in magnitude of a light sensing signal according to an embodiment.

FIG. 16 is a waveform diagram illustrating a change in luminous intensity and a change in magnitude of a light sensing signal according to an embodiment.

Referring to FIG. 16, the main driving circuit 200 may supply a data voltage Data(v) to each of the first through third display pixels SP1 through SP3 and the infrared light emitting pixels ESP by varying the magnitude of the data voltage Data(v) such that the magnitude of the data voltage Data(v) supplied to each of the first through third display pixels SP1 through SP3 and the infrared light emitting pixels ESP in units of at least one frame period gradually increases or decreases in units of at least one frame.

A voltage PPG(V) of each of light sensing signals output from the light sensing pixels LSP in each light sensing period may gradually vary according to the magnitude of the data voltage Data(v) supplied to each of the first through third display pixels SP1 through SP3 and the infrared light emitting pixels ESP.

Figure 17:
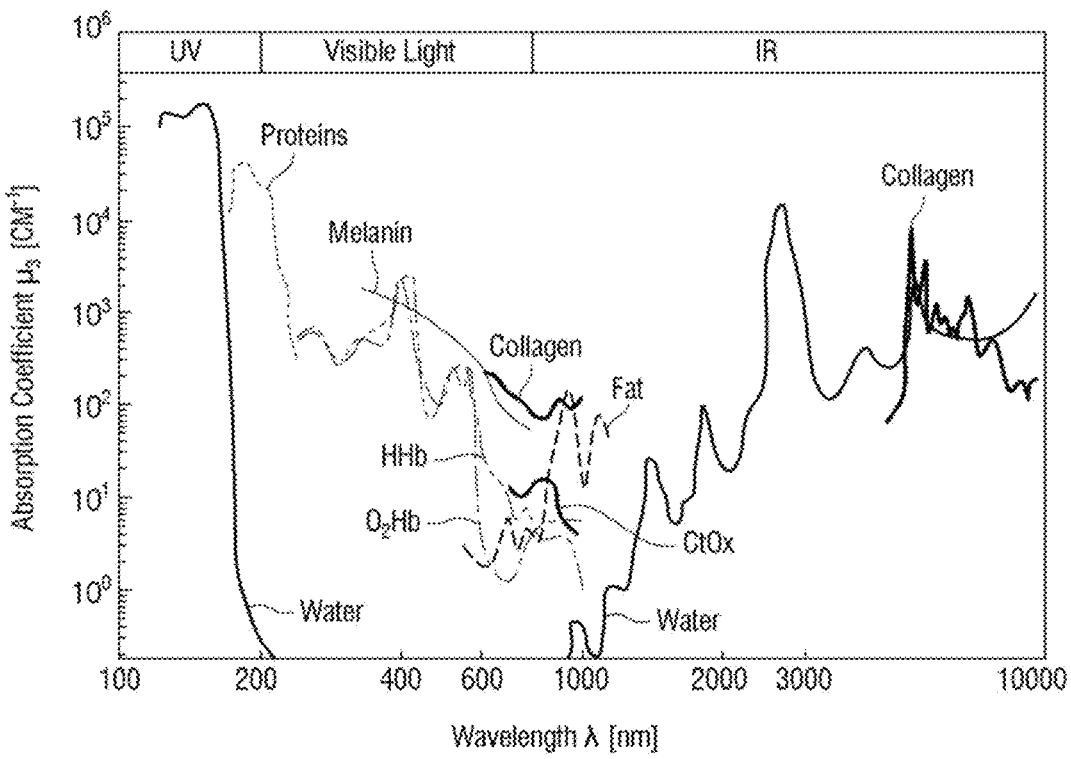
FIG. 17 is a graph illustrating an infrared light absorption coefficient of each object from which a light sensing signal is detected.

FIG. 17 is a graph illustrating an infrared light absorption coefficient of each object from which a light sensing signal is detected.

Referring to FIG. 17, the first through third display pixels SP1 through SP3 and the infrared light emitting pixels ESP may sequentially emit red, green and blue light and infrared light according to data voltages Data(IR) and Data(R). In an embodiment, wavelength bands of infrared light emitted from the first through third display pixels SP1 through SP3 and the infrared light emitting pixels ESP are different from each other. Therefore, the infrared light absorptance and absorption coefficient of each object may vary according to the wavelength band of infrared light emitted from each of the first through third display pixels SP1 through SP3 and the infrared light emitting pixels ESP.

As described above, the display device 10 according to the embodiment may detect light sensing signals of various wavelength bands according to different infrared wavelength bands from various objects such as palms, backs of hands, fingers, scalp, and facial skin. Biomarkers according to protein content, melanin content, collagen content, oxygen saturation, fat mass, obesity, blood pressure, blood flow, etc. may be detected from various objects such as palms, backs of hands, fingers, scalp, and facial skin.

Figure 18:
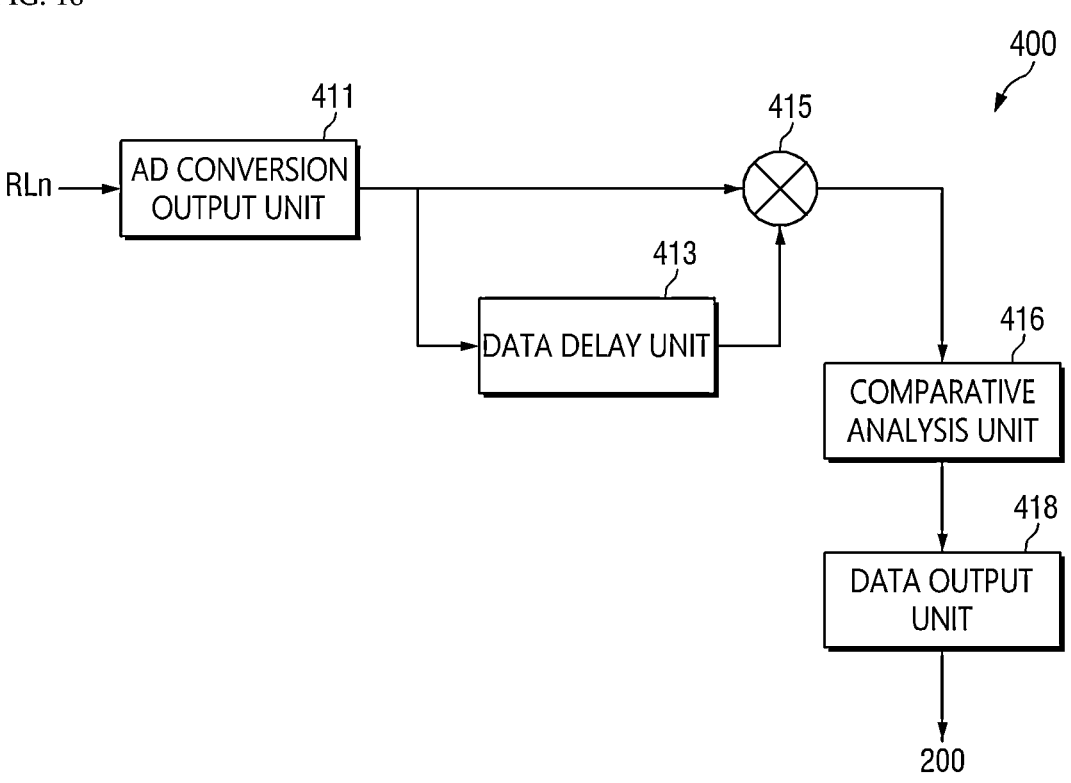
FIG. 18 is a schematic block diagram of a component detection circuit according to an embodiment.

FIG. 18 is a schematic block diagram of a component detection circuit 400 according to an embodiment.

Referring to FIG. 18, the component detection circuit 400 according to the embodiment includes an analog-to-digital (AD) conversion output unit 411 (e.g., an A2D converter), a data delay unit 413 (e.g., a delay circuit), an arithmetic processing unit 415, a comparative analysis unit 416 (e.g., a logic circuit), and a data output unit 418 (e.g., a data output circuit).

The AD conversion output unit 411 converts a light sensing signal from at least one light sensing pixel LSP into a digital light sensing signal.

The data delay unit 413 may include a storage circuit such as at least one flip-flop or a register circuit for storing, delaying and outputting a digital light sensing signal output from the AD conversion output unit 411 in units of at least one horizontal line or frame.

The arithmetic processing unit 415 performs an arithmetic operation on a digital light sensing signal output from the AD conversion output unit 411 and a delayed digital light sensing signal output from the data delay unit 413 and outputs the result value of the arithmetic operation as biometric data. The arithmetic operation may be performed in real time using a preset operation. For example, the arithmetic processing unit 415 performs an arithmetic operation on a digital light sensing signal output in real time from the AD conversion output unit 411 and a delayed digital light sensing signal output from the data delay unit 413 using a preset operation method such as multiplication, addition, subtraction or division or according to a preset mathematical equation and then outputs the result value of the arithmetic operation as biometric data.

The comparative analysis unit 416 compares the biometric data output from the arithmetic processing unit 415 with a preset biomarker data and detects biomarker information similar to the preset biomarker data within a preset error range. The comparison may be performed in real time. The biomarker information detected as a result of the comparison is transmitted to the data output unit 418.

The data output unit 418 shares the biomarker information output from the comparative analysis unit 416 with the main driving circuit 200. Here, the biomarker information may be biomarker information according to protein content, melanin content, collagen content, oxygen saturation, fat mass, obesity, blood pressure, blood flow, etc.

Figure 19:
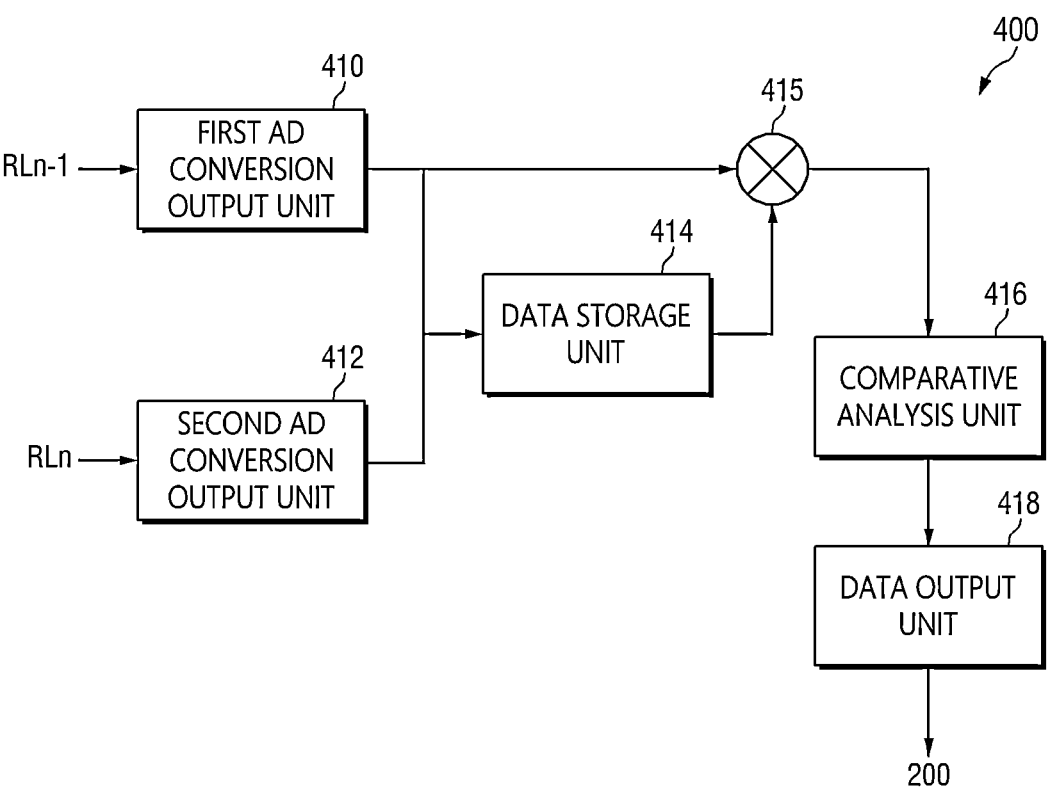
FIG. 19 is a schematic block diagram of a component detection circuit according to an embodiment.

FIG. 19 is a schematic block diagram of a component detection circuit 400 according to an embodiment.

Referring to FIG. 19, the component detection circuit 400 according to the embodiment includes a first AD conversion output unit 410 (e.g., $1^{st}$ A2D converter), a second A2D conversion output unit 412 (e.g., $2^{nd}$ A2D converter), a data storage unit 414, an arithmetic processing unit 415, a comparative analysis unit 416, and a data output unit 418.

The first AD conversion output unit 410 converts a first light sensing signal received from each of the light sensing pixels LSP of the first reflected light sensing area FSA1 into a digital first light sensing signal and outputs the digital first light sensing signal.

The second AD conversion output unit 412 converts a second light sensing signal from each of the light sensing pixels LSP of the second reflected light sensing area FSA2 into a digital second light sensing signal and outputs the digital second light sensing signal.

The data storage unit 414 stores, delays, and outputs at least one of the digital first and second light sensing signals in units of at least one horizontal line or frame. To this end, the data storage unit 414 may include a storage circuit such as at least one flip-flop or a register circuit.

The arithmetic processing unit 415 performs an arithmetic operation on a digital light sensing signal output (e.g., in real time) from the first AD conversion output unit 410 and at least one of the delayed first and second light sensing signals output from the data storage unit 414 (e.g., using a preset operation method) and outputs the result value of the arithmetic operation as biometric data. For example, the arithmetic processing unit 415 performs an arithmetic operation on a digital light sensing signal from the first AD conversion output unit 410 and at least one of the delayed first and second light sensing signals output from the data storage unit 414 using a preset operation method such as multiplication, addition, subtraction or division or according to a preset mathematical equation and then outputs the result value of the arithmetic operation as bio data.

The comparative analysis unit 416 compares the biometric data output (e.g., in real time) from the arithmetic processing unit 415 with preset biomarker data and detects biomarker information similar to the preset biomarker data within a preset error range. The biomarker information detected as a result of the comparison is transmitted to the data output unit 418.

The data output unit 418 shares the biomarker information output from the comparative analysis unit 416 with the main driving circuit 200. Here, the biomarker information may be biomarker information according to protein content, melanin content, collagen content, oxygen saturation, fat mass, obesity, blood pressure, blood flow, etc.

FIG. 20 is a schematic block diagram of a component detection circuit 400 according to an embodiment.

Referring to FIG. 20, the component detection circuit 400 according to the embodiment may further include a biomarker matching unit 420 (e.g., a logic circuit), a database 422, and an authentication result transmission unit 424 (e.g., a transmitter).

The biomarker matching unit 420 compares biomarker information from the data output unit 418 with a users' biomarker information stored in advance in the database 422 and extracts user information in which the biomarker information matches the users' biomarker information within a preset error range. The user's biomarker information may be stored outside the database 422 or in a storage device accessible to the system via a computer network.

The authentication result transmission unit 424 shares the user information in which the biomarker information matches the users' biomarker information with the main driving circuit 200. By extracting the user information as a result of comparing the biomarker information from the data output unit 418 with the users' biomarker information stored in advance in the database 422, it is possible to detect information about a user from which a biomarker has been detected using the display device 10. In addition, the user can be authenticated using the user information.

Figure 21:
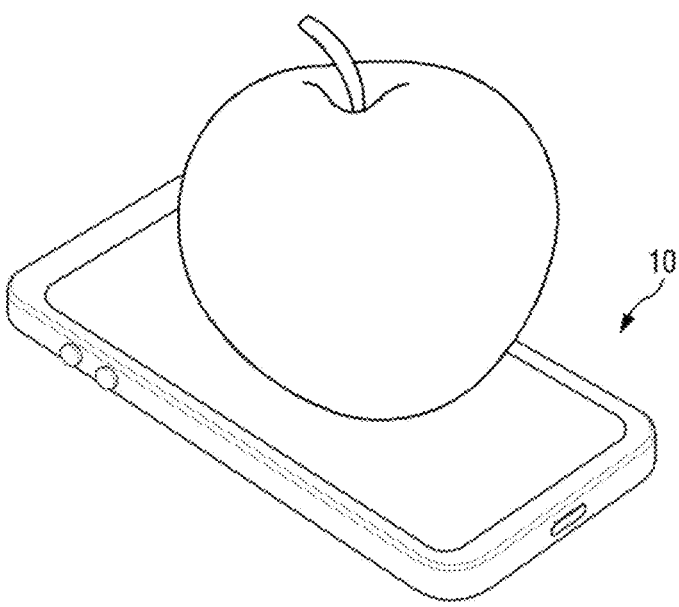
FIG. 21 illustrates a method of measuring sugar content using the display device according to the embodiment.

FIG. 21 illustrates a method of measuring sugar content using the display device 10 according to the embodiment.

Referring to FIG. 21, if an object (e.g., a fruit or a vegetable) is placed on a surface of the display device 10, each of the infrared light emitting pixels ESP arranged in the display area DA of the display device 10 may receive a data voltage of a data wiring DL according to a display scan signal and an emission control signal of the display scan driver 110 and emit light by supplying a driving current to a light emitting element LEL according to the data voltage.

In an embodiment, each of the light sensing pixels LSP arranged in the display area DA generates a light sensing signal corresponding to the amount of reflected light incident from the front side and outputs the light sensing signal to a light sensing signal wiring ERL in response to a sensing scan signal from the light sensing scan driver 120. For example, the object may be placed in front of the display device 10, the emitted light may hit the object, and light reflected off a surface of the object due to the emitted light may be received by the light sensing pixels LSP. Each of the light sensing pixels LSP may sense reflected light in an infrared wavelength band incident from the front side, for example, light in a band ranging from 610 nm to 900 nm or ranging from about 610 nm to about 900 nm according to the emission wavelength band of the infrared light emitting pixels ESP and output a light sensing signal to a light sensing signal wiring ERL.

The component detection circuit 400 modulates the light sensing signals of the light sensing pixels LSP respectively received through the light sensing signal wirings ERL into digital light sensing signals. Then, the digital light sensing signals are analyzed using a preset component analysis algorithm or component analysis program to generate and store component detection data. For example, the component detection circuit 400 may analyze the water content, acidity, chromaticity, chlorophyll, hardness, etc. of fruit, vegetables, coffee beans, etc. according to magnitude values of the light sensing signals by comparing the component detection data including the magnitude values of the light sensing signals with preset comparison data.

Specifically, since the absorbance and reflectance of infrared light vary according to the water content, acidity, chromaticity, chlorophyll, hardness, etc. of fruit, vegetables, coffee beans, etc., the water content, acidity, chromaticity, chlorophyll, hardness, etc. of the fruit, vegetables, coffee beans, etc. can be analyzed according to the magnitude values of the light sensing signals.

Figure 22:
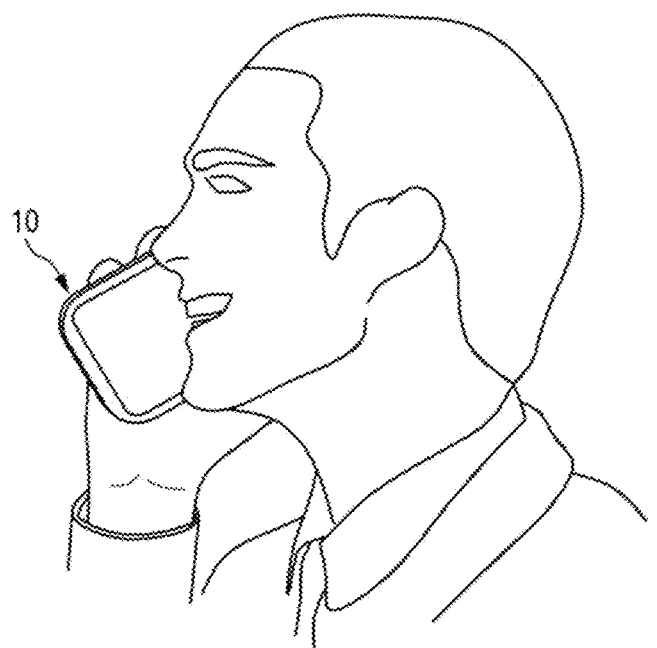
FIG. 22 illustrates a method of measuring a skin moisture level using the display device according to the embodiment.

FIG. 22 illustrates a method of measuring a skin moisture level using the display device 10 according to the embodiment.

Referring to FIG. 22, in a phone call state, each of the light sensing pixels LSP arranged in the display area DA generates a light sensing signal corresponding to the amount of reflected light incident from the front side and outputs the light sensing signal to a light sensing signal wiring ERL in response to a sensing scan signal from the light sensing scan driver 120. Each of the light sensing pixels LSP may sense reflected light in an infrared wavelength band incident from the front side, for example, light in a band ranging from 610 nm to 900 nm or ranging from about 610 nm to about 900 nm according to the emission wavelength band of the infrared light emitting pixels ESP and output a light sensing signal to a light sensing signal wiring ERL.

The component detection circuit 400 modulates the light sensing signals of the light sensing pixels LSP respectively received through the light sensing wirings ERL into digital light sensing signals. Then, the digital light sensing signals are analyzed using a preset component analysis algorithm or component analysis program to generate and store biomarker information. For example, the component detection circuit 400 may analyze skin condition information such as skin moisture level, the amount of sebum, fat layer thickness, and the amount of melanin by comparing the biomarker information with pre-stored biomarker information. Specifically, since the absorbance and reflectance of infrared light vary according to skin conditions such as skin moisture level, the amount of sebum, fat layer thickness and the amount of melanin, the skin condition information such as the skin moisture level, the amount of sebum, fat layer thickness and the amount of melanin can be analyzed according to magnitude values of the light sensing signals.

Figure 23:
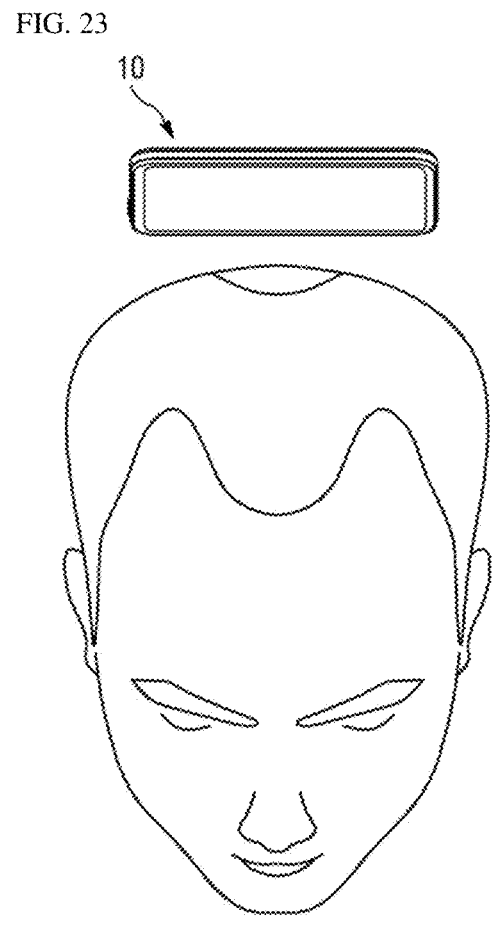

FIG. 23 illustrates a scalp inspection method using the display device 10 according to the embodiment.

Referring to FIG. 23, when the display device 10 is placed above the scalp, each of the light sensing pixels LSP may emit infrared light to inspect scalp conditions. Here, each of the light sensing pixels LSP may sense reflected light in an infrared wavelength band incident from the front side and output a light sensing signal to a light sensing signal wiring ERL.

The component detection circuit 400 generates and stores biomarker information by analyzing the light sensing signals using a preset component analysis algorithm or component analysis program. For example, the component detection circuit 400 may analyze scalp information such as moisture and oiliness levels of the scalp, the size of pores and the amount of sebum according to the biomarker information by comparing the biomarker information including magnitude values of the light sensing signals with preset biomarker information. Specifically, since the absorbance and reflectance of infrared light vary according to scalp conditions such as moisture and oiliness levels of the scalp, the size of pores and the amount of sebum, the scalp condition information such as the moisture and oiliness levels of the scalp, the size of pores and the amount of sebum can be analyzed according to the magnitude values of the light sensing signals.

Figure 24:
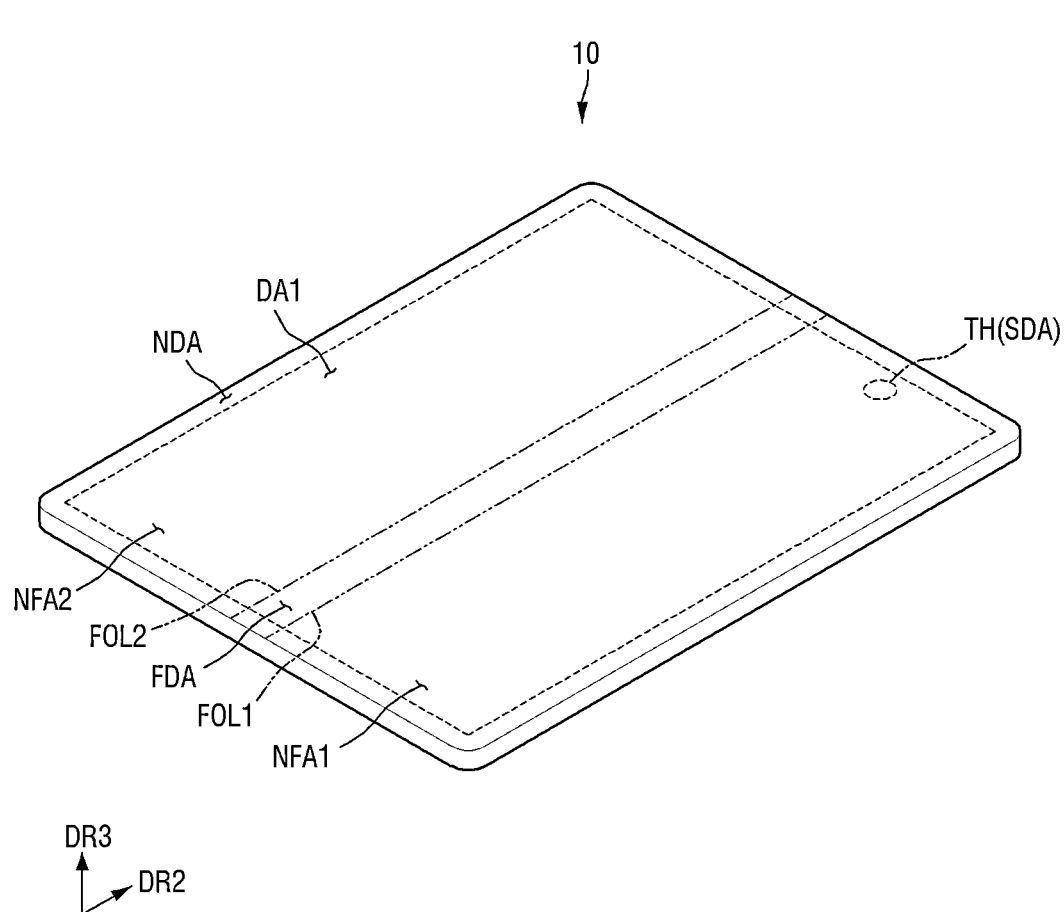
FIGS. 24 and 25 are perspective views of a display device according to an embodiment.
Figure 24:
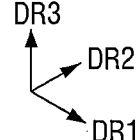
Figure 25:
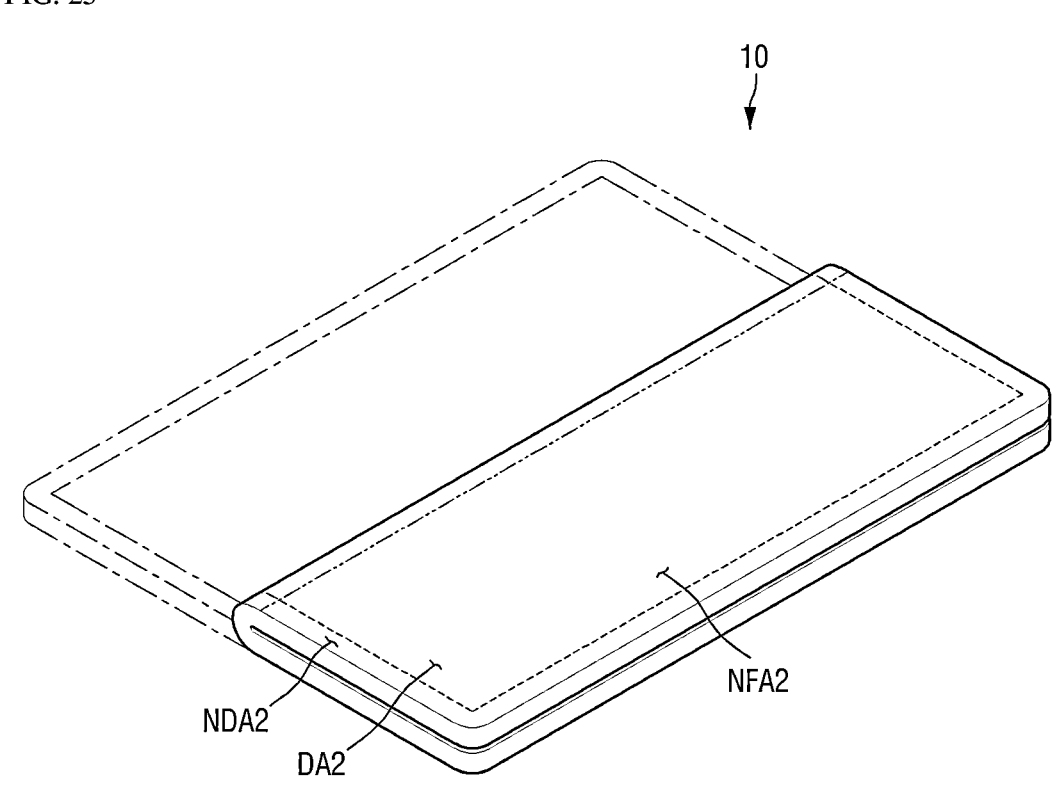
Figure 25:
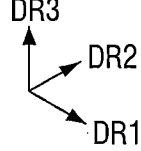

FIGS. 24 and 25 are perspective views of a display device 10 according to an embodiment.

In FIGS. 24 and 25, the display device 10 is illustrated as a foldable display device that is folded in the first direction DR1. The display device 10 may maintain both a folded state and an unfolded state. The display device 10 may be folded in an in-folding manner in which its front surface is disposed inside. When the display device 10 is bent or folded in the in-folding manner, portions of the front surface of the display device 10 may face each other. Alternatively, the display device 10 may be folded in an out-folding manner in which its front surface is disposed outside. When the display device 10 is bent or folded in the out-folding manner, portions of a rear surface of the display device 10 may face each other.

A first non-folding area NFA1 may be disposed on a side, e.g., a right side of a folding area FDA. A second non-folding area NFA2 may be disposed on the other side, e.g., a left side of the folding area FDA. A touch sensing unit TSU according to an embodiment of the present specification may be formed and disposed in each of the first non-folding area NFA1 and the second non-folding area NFA2.

A first folding line FOL1 and a second folding line FOL2 may extend in the second direction DR2, and the display device 10 may be folded in the first direction DR1. Therefore, since a length of the display device 10 in the first direction DR1 can be reduced to about half, a user can easily carry the display device 10.

The first folding line FOL1 and the second folding line FOL2 may not necessarily extend in the second direction DR2. For example, the first folding line FOL1 and the second folding line FOL2 may extend in the first direction DR1, and the display device 10 may be folded in the second direction DR2. In this case, a length of the display device 10 in the second direction DR2 may be reduced to about half. Alternatively, the first folding line FOL1 and the second folding line FOL2 may extend in a diagonal direction of the display device 10 between the first direction DR1 and the second direction DR2. In this case, the display device 10 may be folded in a triangular shape.

When the first folding line FOL1 and the second folding line FOL2 extend in the second direction DR2, a length of the folding area FDA may be smaller in the first direction DR1 than in the second direction DR2. In addition, a length of the first non-folding area NFA1 in the first direction DR1 may be greater than the length of the folding area FDA in the first direction DR1. A length of the second non-folding area NFA2 in the first direction DR1 may be greater than the length of the folding area FDA in the first direction DR1.

A first display area DA1 may be disposed on the front surface of the display device 10. The first display area DA1 may overlap the folding area FDA, the first non-folding area NFA1, and the second non-folding area NFA2. Therefore, when the display device 10 is unfolded, an image may be displayed in a forward direction on the folding area FDA, the first non-folding area NFA1, and the second non-folding area NFA2 of the display device 10.

A second display area DA2 may be disposed on the rear surface of the display device 10. The second display area DA2 may overlap the second non-folding area NFA2. Therefore, when the display device 10 is folded, an image may be displayed in the forward direction on the second non-folding area NFA2 of the display device 10.

Although a through hole TH in which a camera SDA or the like is formed is disposed in the first non-folding area NFA1 in FIGS. 24 and 25, the present disclosure is not limited thereto.

The through hole TH or the camera SDA may also be disposed in the second non-folding area NFA2 or the folding area FDA.

In the through hole TH, at least one infrared light emitting element emitting infrared light and at least one light sensing element (not illustrated) receiving infrared reflected light may be further formed. Accordingly, infrared light may be emitted by the at least one infrared light emitting element, and reflected light in an infrared wavelength band incident from a front side may be sensed through the at least one light sensing element.

A component detection circuit 400 may analyze light sensing signals using a preset component analysis algorithm or component analysis program and generate biomarker information according to magnitude values of the light sensing signals.

In display devices according to embodiments, when light emitted from red, green and blue subpixels and infrared light emitting pixels is reflected by an object such as a body part, the reflected light may be sensed using light sensing pixels of a display panel to detect optical signals. Then, the detected optical signals may be analyzed to extract various biomarkers of the object.

In addition, a display device according to an embodiments emits infrared light of different wavelength bands and extracts various biomarkers by detecting infrared optical signals of various wavelength bands. Therefore, application fields and utilization of the display devices can be further increased.

However, the effects of the present disclosure are not restricted to the one set forth herein.

In concluding the detailed description, those skilled in the art will appreciate that many variations and modifications can be made to the these embodiments without substantially departing from the principles of the present invention. Therefore, the disclosed embodiments of the invention are used in a generic and descriptive sense only and not for purposes of limitation.

What is claimed is:

1. A display device comprising:
display pixels arranged in a display area of a display panel;
infrared light emitting pixels arranged in the display area to alternate with the display pixels along a diagonal direction relative to intersecting first and second directions;
light sensing pixels arranged in the display area to alternate with the infrared light emitting pixels along the first direction and the second direction, wherein the light sensing pixels detect light sensing signals based on reflected light reflected from an object in front of the display panel;
a display scan driver supplying display scan signals to the display pixels and the infrared light emitting pixels;
a light sensing driver sequentially supplying sensing scan signals to the light sensing pixels; and
a component detection circuit for generating biomarker information using the light sensing signals received from the light sensing pixels.

2. The display device of claim 1, wherein the display area comprises:
an image display area in which only the display pixels are disposed without the infrared light emitting pixels and the light sensing pixels; and
at least one reflected light sensing area in which the display pixels, the infrared light emitting pixels, and the light sensing pixels are alternately disposed.

3. The display device of claim 2, where the image display area completely surrounds the reflected light sensing area.

4. The display device of claim 3, wherein in the display area, first and second display pixels respectively displaying red light and green light among the display pixels, one infrared light emitting pixel and one light sensing pixel are arranged to form a first unit pixel, and second and third display pixels respectively displaying green light and blue light among the display pixels, one infrared light emitting pixel and one light sensing pixel are arranged to form a second unit pixel.

5. The display device of claim 4, wherein the first and second unit pixels are alternately arranged in a zigzag pattern along the first direction and the second direction or are alternately arranged in a matrix along the first direction and the second direction.

6. The display device of claim 3, wherein the light sensing pixels generate the light sensing signals corresponding to amounts of the reflected light incident and transmit the light sensing signals to the component detection circuit by sequentially responding to the display scan signals received from the display scan driver through display scan wirings.

7. The display device of claim 3, wherein the component detection circuit comprises:
a first analog-to-digital (A2D) converter converting a first light sensing signal received from each light sensing pixel in a first reflected light sensing area of the display area into a digital first light sensing signal;
a second A2D converter converting a second light sensing signal from each light sensing pixel in a second reflected light sensing area of the display area into a digital second light sensing signal;
a delay circuit storing, delaying, and outputting at least one of the digital first and second light sensing signals in units of at least one horizontal line or frame;
an arithmetic processing unit generating biometric data by performing an arithmetic operation on a digital light sensing signal output from the first A2D converter and at least one of the delayed first and second light sensing signals output from the delayed circuit; and
a logic circuit comparing the biometric data with preset biomarker data to generate a comparison result and detecting the biomarker information using the comparison result.

8. A display device comprising:
display pixels arranged in a display area of a display panel;
infrared light emitting pixels arranged in the display area to alternate with the display pixels;
light sensing pixels arranged in the display area to alternate with the infrared light emitting pixels, wherein the light sensing pixels detect light sensing signals based on reflected light reflected from an object;
a display scan driver supplying display scan signals to the display pixels and the infrared light emitting pixels;
a light sensing driver sequentially supplying sensing scan signals to the light sensing pixels;
a component detection circuit for generating biomarker information using the light sensing signals received from the light sensing pixels;
a touch sensing circuit for detecting coordinate data of a touch position of a user through touch electrodes of a touch sensor; and
a main driving circuit controlling driving timings of the display pixels, the light emitting pixels, the light sensing driver, and the display scan driver,
wherein the display area comprises:
an image display area in which only the display pixels are disposed without the infrared light emitting pixels and the light sensing pixels; and
a first reflected light sensing area in which the infrared light emitting pixels are arranged to alternate with the display pixels along a first diagonal row extending diagonally relative to a first direction of the display panel, and the light sensing pixels are arranged to alternate with the display pixels along a second diagonal row adjacent to the first diagonal row, where the image display area completely surrounds the reflected light sensing area.

9. The display device of claim 8, wherein in the display area, first and second display pixels respectively displaying red light and green light among the display pixels, one infrared light emitting pixel and one light sensing pixel are arranged to form a first unit pixel, and second and third display pixels respectively displaying green light and blue light among the display pixels, one infrared light emitting pixel and one light sensing pixel are arranged to form a second unit pixel.

10. The display device of claim 9, wherein the first and second unit pixels are alternately arranged in a zigzag pattern along the first direction and a second direction or are alternately arranged in a matrix along the first direction and the second direction.

11. The display device of claim 8, wherein the light sensing pixels generate the light sensing signals corresponding to amounts of the reflected light incident and transmit the light sensing signals to the component detection circuit by sequentially responding to the display scan signals received from the display scan driver through display scan wirings.

12. The display device of claim 8, wherein the component detection circuit comprises:

a first analog-to-digital (A2D) converter converting a first light sensing signal received from each light sensing pixel in a first reflected light sensing area of the display area into a digital first light sensing signal;

a second A2D converter converting a second light sensing signal from each light sensing pixel in a second reflected light sensing area of the display area into a digital second light sensing signal;

a delay circuit storing, delaying, and outputting at least one of the digital first and second light sensing signals in units of at least one horizontal line or frame;

an arithmetic processing unit generating biometric data by performing an arithmetic operation on a digital light sensing signal output from the first A2D converter and at least one of the delayed first and second light sensing signals output from the delayed circuit; and a logic circuit comparing the biometric data with preset biomarker data to generate a comparison result and detecting the biomarker information using the comparison result.

13. An electronic device including a display device, the display device comprising:

display pixels arranged in a display area of a display panel;

infrared light emitting pixels arranged in the display area to alternate with the display pixels along a diagonal direction relative to intersecting first and second directions;

light sensing pixels arranged in the display area to alternate with the infrared light emitting pixels along the first direction and the second direction, wherein the light sensing pixels detect light sensing signals based on reflected light reflected from an object;

a display scan driver supplying display scan signals to the display pixels and the infrared light emitting pixels;

a light sensing driver sequentially supplying sensing scan signals to the light sensing pixels; and a component detection circuit for generating biomarker information using the light sensing signals received from the light sensing pixels.

14. The electronic device of claim 13, wherein the display area comprises:

an image display area in which only the display pixels are disposed without the infrared light emitting pixels and the light sensing pixels; and at least one reflected light sensing area in which the display pixels, the infrared light emitting pixels, and the light sensing pixels are alternately disposed.

15. The electronic device of claim 14, where the image display area completely surrounds the reflected light sensing area.

16. The electronic device of claim 15, wherein in the display area, first and second display pixels respectively displaying red light and green light among the display pixels, one infrared light emitting pixel and one light sensing pixel are arranged to form a first unit pixel, and second and third display pixels respectively displaying green light and blue light among the display pixels, one infrared light emitting pixel and one light sensing pixel are arranged to form a second unit pixel.

17. The electronic device of claim 16, wherein the first and second unit pixels are alternately arranged in a zigzag pattern along the first direction and the second direction or are alternately arranged in a matrix along the first direction and the second direction.

18. The electronic device of claim 15, wherein the light sensing pixels generate the light sensing signals corresponding to amounts of the reflected light incident and transmit the light sensing signals to the component detection circuit by sequentially responding to the display scan signals received from the display scan driver through display scan wirings.

19. The electronic device of claim 13, wherein the component detection circuit comprises:

a first analog-to-digital (A2D) converter converting a first light sensing signal received from each light sensing pixel in a first reflected light sensing area of the display area into a digital first light sensing signal;

a second A2D converter converting a second light sensing signal from each light sensing pixel in a second reflected light sensing area of the display area into a digital second light sensing signal;

a delay circuit storing, delaying, and outputting at least one of the digital first and second light sensing signals in units of at least one horizontal line or frame;

an arithmetic processing unit generating biometric data by performing an arithmetic operation on a digital light sensing signal output from the first A2D converter and at least one of the delayed first and second light sensing signals output from the delayed circuit; and a logic circuit comparing the biometric data with preset biomarker data to generate a comparison result and detecting the biomarker information using the comparison result.

20. The electronic device of claim 13, wherein the display area comprises:

an image display area in which only the display pixels are disposed without the infrared light emitting pixels and the light sensing pixels; and at least one reflected light sensing area in which the display pixels, the infrared light emitting pixels, and the light sensing pixels are alternately disposed, where the image display area completely surrounds the reflected light sensing area.

\* \* \* \* \*